United States Patent
Cherubini et al.

(10) Patent No.: US 9,956,559 B2
(45) Date of Patent: *May 1, 2018

(54) INSTRUMENT AND METHOD FOR THE AUTOMATED THERMAL TREATMENT OF LIQUID SAMPLES

(71) Applicant: ROCHE MOLECULAR SYSTEMS, INC., Pleasanton, CA (US)

(72) Inventors: Claudio Cherubini, Cham (CH); Roger Iten, Ebikon (CH); Emad Sarofim, Hagendorn (CH); Kurt Schildknecht, Huenenberg (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/385,020

(22) Filed: Dec. 20, 2016

(65) Prior Publication Data

US 2017/0100715 A1 Apr. 13, 2017

Related U.S. Application Data

(63) Continuation of application No. 14/243,524, filed on Apr. 2, 2014, now Pat. No. 9,557,269.

(51) Int. Cl.
*G01N 1/10* (2006.01)
*B01L 3/00* (2006.01)
(Continued)

(52) U.S. Cl.
CPC ....... *B01L 3/50851* (2013.01); *B01L 3/50853* (2013.01); *B01L 7/52* (2013.01);
(Continued)

(58) Field of Classification Search
CPC ... G01N 2021/6482; G01N 2021/6484; G01N 21/6452; G01N 21/645; C12Q 1/686
(Continued)

(56) References Cited

U.S. PATENT DOCUMENTS 3,636,366 A 1/1972 Sheldon
4,683,195 A 7/1987 Mullis
(Continued)

FOREIGN PATENT DOCUMENTS

DE 102006036017 2/2008
EP 0902271 3/1999
(Continued)

OTHER PUBLICATIONS

European Search Report issued by the European Patent Office, dated Jun. 13, 2013, for related European Patent Application No. 13162185.6; 6 pages.
(Continued)

*Primary Examiner* — Hoa Pham
(74) *Attorney, Agent, or Firm* — Faegre Baker Daniels LLP

(57) ABSTRACT

An instrument and a method for the automated thermal treatment of liquid samples are disclosed. An inter-distance between a temperature-controlled receptacle for loading with a plurality of vessels for containing the samples and end portions of optical fibers can be varied, wherein the receptacle is configured to form a thermal communication with the loaded vessels and wherein the optical fibers have first and second end portions. The first end portion and the second end portion of each optical fiber is fixed with respect to each other for transmitting light, wherein the variation of the in-ter-distance allows the vessels to be loaded to or unloaded from the receptacle and to enable detection of light from the samples contained in the one or more receptacle-loaded vessels.

17 Claims, 20 Drawing Sheets

(51) Int. Cl.
  *B01L 7/00* (2006.01)
  *C12Q 1/68* (2018.01)
  *G01N 35/02* (2006.01)
  *G01N 21/64* (2006.01)
  *G01N 21/25* (2006.01)
  *G01N 35/00* (2006.01)

(52) U.S. Cl.
  CPC .......... *C12Q 1/686* (2013.01); *G01N 21/253* (2013.01); *G01N 21/6452* (2013.01); *G01N 35/028* (2013.01); *B01L 2200/022* (2013.01); *B01L 2300/041* (2013.01); *B01L 2300/0654* (2013.01); *B01L 2300/0829* (2013.01); *B01L 2300/1805* (2013.01); *G01N 2021/6484* (2013.01); *G01N 2035/00376* (2013.01)

(58) Field of Classification Search
  USPC .......... 356/244, 246, 440; 422/82.05; 435/6, 435/91.1, 91.2; 436/517, 526, 536
  See application file for complete search history.

(56) References Cited

U.S. PATENT DOCUMENTS

| | | | |
|---|---|---|---|
| 4,683,303 A | 7/1987 | Pfaendler | |
| 4,800,159 A | 1/1989 | Mullis | |
| 4,944,922 A * | 7/1990 | Hayashi | G01N 35/1009 356/624 |
| 4,965,188 A | 10/1990 | Mullis | |
| 5,589,351 A | 12/1996 | Harootunian | |
| 5,830,134 A | 11/1998 | Caputo | |
| 6,015,674 A | 1/2000 | Woudenberg | |
| 6,144,448 A | 11/2000 | Mitoma | |
| 6,197,572 B1 | 3/2001 | Schneebeli | |
| 6,569,631 B1 | 5/2003 | Pantoliano | |
| 6,814,934 B1 | 11/2004 | Higuchi | |
| 7,139,075 B2 | 11/2006 | Molter | |
| 8,778,696 B2 * | 7/2014 | Gutmann | B01L 3/5027 422/501 |
| 8,797,526 B2 | 8/2014 | Cherubini | |
| 9,557,269 B2 * | 1/2017 | Cherubini | B01L 7/52 |
| 2002/0030044 A1 | 3/2002 | Brown | |
| 2002/0037526 A1 | 3/2002 | Tashiro | |
| 2003/0038248 A1 | 2/2003 | Maher | |
| 2006/0093254 A1 | 5/2006 | Mozdy | |
| 2007/0098594 A1 | 5/2007 | Elkin | |
| 2007/0206187 A1 | 9/2007 | Lundquist | |
| 2008/0149851 A1 | 6/2008 | Makiuchi | |
| 2009/0059225 A1 | 3/2009 | Robertson | |
| 2009/0218518 A1 | 9/2009 | Schirr | |
| 2011/0039711 A1 | 2/2011 | Howell | |
| 2012/0014835 A1 * | 1/2012 | Howell | G01N 21/253 422/52 |
| 2012/0190034 A1 | 7/2012 | Tajima | |
| 2013/0228675 A1 | 9/2013 | Chen | |

FOREIGN PATENT DOCUMENTS

| | | |
|---|---|---|
| EP | 0953379 | 11/1999 |
| EP | 0953838 | 11/1999 |
| EP | 1191336 | 3/2002 |
| EP | 2081011 | 7/2009 |
| JP | 63298137 | 12/1988 |
| WO | WO 93/13423 | 7/1993 |
| WO | WO 00/71992 | 11/2000 |
| WO | WO 2003/098279 | 11/2003 |
| WO | WO 2004/024330 | 3/2004 |
| WO | WO 2009/027102 | 3/2009 |
| WO | WO 2010/079338 | 7/2010 |

OTHER PUBLICATIONS

European Search Report issued by the European Patent Office, dated Apr. 11, 2011, for related European Patent Application No. 10191156; 6 pages.

* cited by examiner

INSTRUMENT AND METHOD FOR THE AUTOMATED THERMAL TREATMENT OF LIQUID SAMPLES

PRIORITY

The present application is a continuation application of U.S. patent application Ser. No. 14/243,524, filed Apr. 2, 2014, titled INSTRUMENT AND METHOD FOR THE AUTOMATED THERMAL TREATMENT OF LIQUID SAMPLES, the disclosure of which is hereby incorporated by reference and the priority of which is hereby claimed.

TECHNICAL FIELD

The embodiments of the present invention are in the field of biochemical research, biochemical routine analytics, clinical diagnostics and clinical research and more particularly concerns an instrument and method for the automated thermal treatment and, e.g., fluorescence detection of liquid samples.

BACKGROUND

In these days, nucleic acids (DNA=deoxyribonucleic acid, RNA=ribonucleic acid) are subject to various analyses and assays in the above-described technical field. In order to detect small amounts, the well-known polymerase chain reaction (PCR) can be used to replicate the target nucleic acid sequence to an amount which is detectable. The amplification of nucleic acids using the polymerase chain reaction has been extensively described in the patent literature, for instance, in U.S. Pat. Nos. 4,683,303, 4,683,195, 4,800,159 and 4,965,188. Generally, in the polymerase chain reaction, samples containing reaction mixtures of specific reagents and nucleic acids are repeatedly put through a sequence of amplification steps. Each sequence includes melting the double-stranded nucleic acids to obtain denaturated single polynucleotide strands, annealing short primers to the strands and extending those primers to synthesize new polynucleotide strands along the denaturated strands to make new copies of double-stranded nucleic acids. Due to the fact that reaction conditions strongly vary with temperatures, the samples are put through a series of temperature excursions in which predetermined temperatures are kept constant for specific time intervals ("thermo-cycling"). The temperature of the samples typically is raised to around 90° C. for melting the nucleic acids and lowered to a temperature in the range of from 40° C. to 70° C. for annealing and primer extension along the polynucleotide strands.

It is also known to detect the PCR reaction products during progress of the polymerase chain reaction ("real-time PCR") to detect the presence or absence of a target nucleic acid sequence (or analyte) and/or to quantify the original amount of target nucleic acid which was present in the sample. In daily routine, commercially available instruments are being used for performing the PCR and detecting the reaction products obtained by means of fluorescence.

SUMMARY

In one embodiment, an instrument for the automated thermal treatment of liquid samples is disclosed. The instrument may comprise a temperature-controlled receptacle for loading with a plurality of vessels for containing the samples, the receptacle being configured to form a thermal communication with the loaded vessels. A detection module equipped with a detection arrangement may be provided with one or more detectors for detecting light emitted from the samples and a coupling arrangement provided with a plurality of optical fibers for transmitting the emitted light to the detection arrangement, wherein the optical fibers have first and second end portions, and the first end portion and the second end portion of each optical fiber are fixed with respect to each other. A moving mechanism for moving at least one of the coupling arrangement and the receptacle in a manner to vary an inter-distance between the coupling arrangement and the receptacle is provided so as to allow the vessels to be loaded to or unloaded from the receptacle and to allow detection of light from samples contained in the one or more receptacle-loaded vessels.

In another embodiment, a method for the automated thermal treatment of liquid samples is disclosed. The method may comprise varying an inter-distance between a temperature-controlled receptacle for loading with a plurality of vessels for containing the samples and end portions of optical fibers, wherein the receptacle is configured to form a thermal communication with the loaded vessels and wherein the optical fibers have first and second end portions. The first end portion and the second end portion of each optical fiber are fixed with respect to each other for transmitting light. The variation of the inter-distance allows the vessels to be loaded to or unloaded from the receptacle and to allow detection of light from the samples contained in the one or more receptacle-loaded vessels.

These and other embodiments are disclosed hereafter in the detailed description as well as in the accompanying drawings.

BRIEF DESCRIPTION OF THE DRAWINGS

The accompanying drawings, which are incorporated in and constitute a part of the specification, illustrate certain embodiments of the invention, and in which.

REFERENCE LIST

Figure 1:
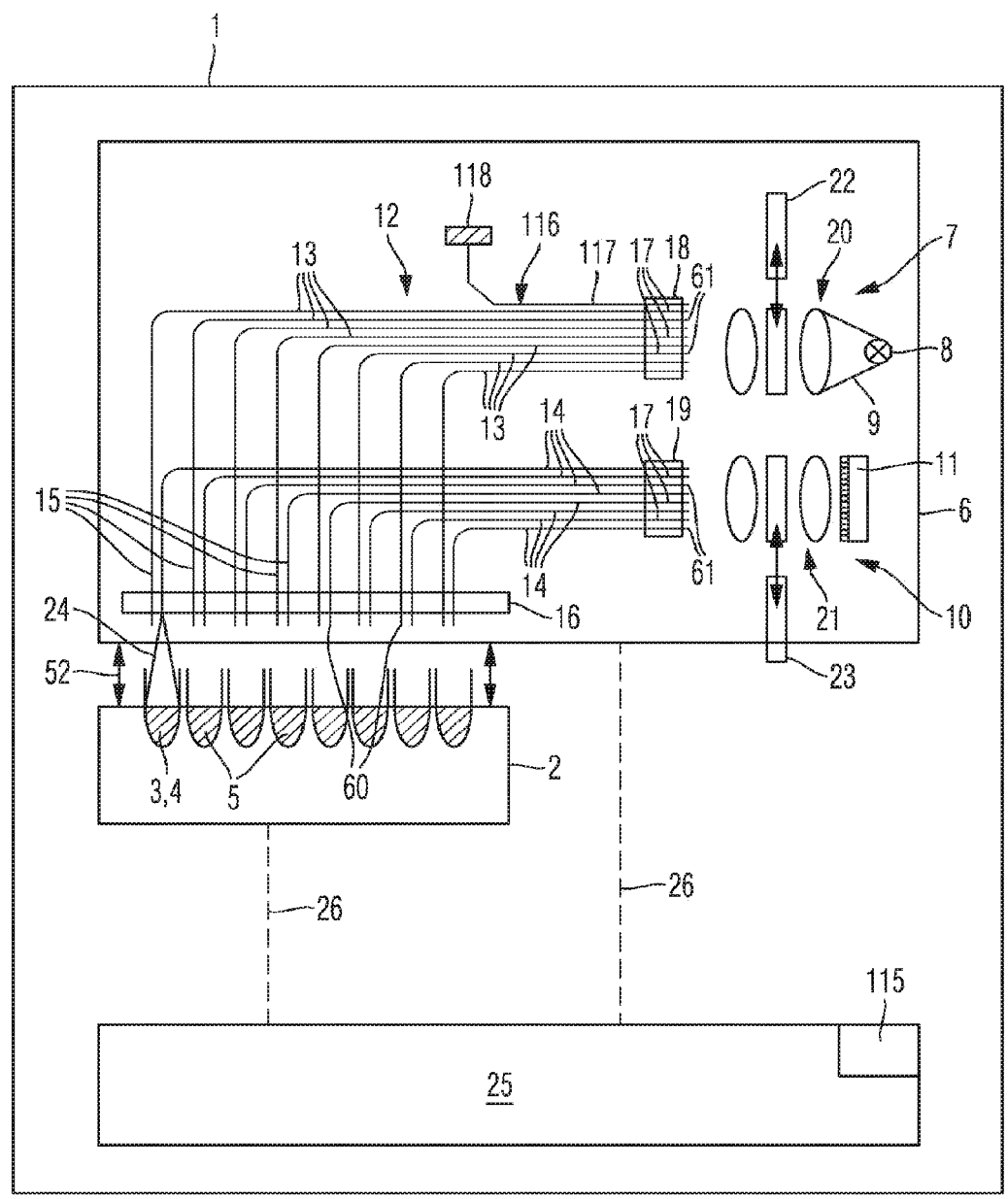
FIG. 1 is a schematic illustration of various modules of exemplary instruments for the automated thermal treating of samples according to the invention.

1 Instrument
2 Thermal module
3 Multi-well plate
4 Well
5 Sample
6 Detection module
7 Excitation arrangement
8 Light source
9 Excitation light
10 Detection arrangement
11 Detector
12 Coupling arrangement
13 Excitation fiber
14 Emission fiber
15 First end portion
16 First fixing element
17 Second end portion
18 Second fixing element
19 Third fixing element
20 Excitation optics
21 Emission optics
22 Excitation filter
23 Emission filter
24 Emitted light
25 Controller
26 Electric lines
27 Thermal block
28 Receptacle
29 Heat exchanger
30 Rib
31 Main base
32 Upper receptacle face
33 Recess
34 Sealing cover
35 Upper plate face
36 Lower plate face
37 Contact face
38 Chassis
39 Vertical plate
40 Upper horizontal plate
41 Lower horizontal plate
42 First through-hole
43 First opening
44 Second opening
45 Second through-hole
46 Third through-hole
47 First casing
48 Dichroic mirror
49 Second casing
50 Filter wheel
51 Electric motor
52 Moving mechanism
53 Rail
54 Free space
55 Thermoelectric device
56 Cylindrical portion
57 Disk-like portion
58 Projection
59 Orifice
60 First end face
61 Second end face
62 Hollow
63 Adhesive material
64 Cover heater
65 Heating element
66 Heating plate
67 Plate hole
68 Cavity
69 Upper plate face
70 Element hole
71 Contact region
72 Planar portion
73 Lower planar portion face
74 Upper heating element face
75 Upper horizontal plate face
76 Core
77 Coating
78 Cover heater hole
79 Mapping device
80 Base
81 Light generating element
82 Control panel
83 First turn-switch
84 Second turn-switch
85 Device controller
86 Electric line
87 Upper base face
88 Contact area
89 Base
90 Instrument casing
91 Lever
92 Fulcrum
93 Upper lever portion
94 Lower lever portion
95 Upper end
96 Connecting rod
97 Turning knuckle
98 First arm
99 Second arm
100 Guiding rod
101 Coil spring
102 Tray
103 Supporting base
104 Beam
105 Front cover
106 Recessed grip
107 Spring catch
108 Opening/closing device
109 Central axis
110 Lower end
112 Projection
113 Guiding rail
114 Resting portion
115 Data storage
116 Reference channel
117 Reference channel fiber
118 Reference channel detector
119 Flange
120 Screw
121 Mounting hole
122 Interface layer
123 Clamp 124 Isolation block
125 Base plate
126 Arm
127 Middle portion
128 Gripping portion
129 Clamping mechanism
130 Gripping recess

DETAILED DESCRIPTION

According to a first aspect, a new instrument for the automated thermal treatment of liquid samples is disclosed. In some embodiments, the instrument is being used for the execution of the PCR, in particular real-time PCR. Specifically, in some embodiments, the instrument is being used for PCR with hybridization probes, PCR with hydrolysis probes, PCR with interchelator dyes, real-time PCR with corresponding probes, various isothermal amplification methods with corresponding fluorescence reporters and melting analysis of DNA. Typical analyses are the detection of the presence/absence and optionally concentration of pathogens such as virus or bacteria in a sample, genotyping, measuring expression profiles, and many others.

In some embodiments, the instrument comprises a temperature-controlled receptacle for receiving a plurality of vessels for containing the liquid samples. The receptacle is being configured to form a thermal communication with the loaded vessels so that samples contained therein are in thermal communication with the receptacle to be heated or cooled according to the specific demands of the user.

In some embodiments, the instrument comprises a detection module equipped with a detection arrangement provided with one or more detectors for detecting light emitted from the liquid samples and a coupling arrangement provided with a plurality of optical fibers for transmitting emitted light to the detection arrangement, wherein said optical fibers have first and second end portions, and wherein, in some embodiments, the first end portion and the second end portion of each optical fiber are being fixed with respect to each other.

In some embodiments, the detection module further comprises an excitation arrangement provided with one or more light sources for generating excitation light. In some embodiments, the one or more detectors are configured for detecting light emitted from the liquid samples in response to the excitation light.

In some embodiments, the instrument comprises a moving mechanism such as, but not limited to, an automated moving mechanism for moving the coupling arrangement and/or the receptacle in a manner to vary an inter-distance between the coupling arrangement and the receptacle so as to allow the vessels to be loaded to or unloaded from the receptacle so that the vessels, i.e., samples contained therein can be brought in and out of thermal communication with the receptacle and to allow the detection of light from samples contained in the one or more receptacle-loaded vessels. In some embodiments, the moving mechanism includes a controllable drive such as, but not limited to, an electric motor or a hydraulic or pneumatic actuator operatively coupled to a guiding mechanism such as, but not limited to, a rack-and-pinion mechanism for automatically moving the coupling arrangement and/or the receptacle so as vary an inter-distance between the coupling arrangement and the receptacle.

In some embodiments, the moving mechanism is configured to move the coupling arrangement while the receptacle is being kept stationary. In some embodiments, the moving module is configured to move the detection module. In some embodiments, the moving mechanism is configured to move the coupling arrangement while the detection arrangement is being kept stationary.

In some embodiments, the optical fibers include first fibers, in the following denoted as "emission fibers" for trans-mitting the emitted light to the detection arrangement and second fibers different from the first fibers, in the following denoted as "excitation fibers" for transmitting excitation light to the samples. In some embodiments, the first end portions of the excitation and emission fibers are being fixed by at least one plate-like fixing element, wherein the second end portions of the excitation and emission fibers are being fixed by at least one another plate-like fixing element. Specifically, in some embodiments, the first end portions of the excitation and emission fibers are being fixed by one first plate-like fixing element, wherein the second end portions of the excitation fibers are being fixed by one second plate-like fixing element and the second end portions of the emission fibers are being fixed by one third plate-like fixing element.

In some embodiments, the coupling arrangement is being equipped with a cover heater for heating a sealing cover placed over a multi-well plate having a plurality of wells for containing the samples. In some embodiments, the cover heater includes a heated plate-like heating member configured to be brought in physical contact with the sealing cover, wherein the heating member is being equipped with a plurality of openings accommodating first end portions of the optical fibers. In some embodiments, the optical fibers are being thermally isolated from the heating member. In some embodiments, the openings are configured to form cavities in case the heating member contacts the multi-well plate, wherein the cavities are being adapted to optically shield the wells from each other. In some embodiments, the openings are configured to form closed cavities in case the heating member contacts the multi-well plate. In some embodiments, the heating member is configured to exert mechanical pressure on the multi-well plate so as to press the wells into recesses of the receptacle.

In some embodiments, the instrument includes a controller set up to control the instrument for the thermal treatment of samples. In some embodiments, the controller is configured as programmable logic controller running a machine-readable program provided with instructions to perform operations for thermally treating the liquid samples. Stated more particularly, in some embodiments, the controller is electrically connected to the components requiring control. In some embodiments, the controller is set up to perform a step of varying an inter-distance between the temperature-controlled receptacle and the first end portions of the optical fibers. In some embodiments, the controller is set up to perform a step of moving the optical fibers with respect to the receptacle while keeping the receptacle stationary. In some embodiments, the controller is set up to perform a step of commonly moving the optical fibers and the detection arrangement with respect to the receptacle while keeping the receptacle stationary. In some embodiments, the controller is designed to execute the fluorescence detection of the samples, including control of at least one light source, position of filter wheels, operation of one or more detectors and data processing.

In some embodiments, the instrument includes or may access a volatile or non-volatile data storage storing an end-to-end relationship (mapping) between the first end portion and the second end portion of individual optical fibers so that the second end portion of each optical fiber can be assigned to the first end portion thereof in a one-to-one relationship. The mapping in particular concerns the position of the first end portion in terms of from which vessel light is received, that is to say, each optical fiber is positioned to receive light from a specific sample vessel located beneath. The second end portions have a stochastic lateral position and light from the second ends is received by a laterally-resolving detector. Due to the end-to-end mapping, it is determined in which lateral position light from a particular vessel is received. Accordingly, a signal measured can be related by the end-to-end mapping to a specific sample vessel.

In some embodiments, the coupling arrangement is being provided with the data storage storing the end-to-end relationship (mapping). In some embodiments, the controller relates to measured fluorescence data from an optical sensor array to respective vessels—based on the mapping data in the data storage. Non-volatile data storages are preferred because data can be stored right after the mapping process and the non-volatile data storage can be fixed to the coupling arrangement so that a mix-up and unintended data manipulations can mostly be prevented. Examples for the non-volatile data storage are compact disc (CD), USB-stick, EEPROM, flash memory. The instrument can also be supplied with the end-to-end relationship (mapping) via the internet. Access to the internet can be provided by a LAN or WLAN or UMTS-connection or any other wired or wireless connection technique.

According to a second aspect, a new method for the automated thermal treatment and, e.g., fluorescence detection of liquid samples is disclosed. The method can, e.g., be implemented in the above-described instrument for thermally treating liquid samples.

In some embodiments, the method comprises a step of varying an inter-distance between a temperature-controlled receptacle for loading with a plurality of vessels for containing the samples and end portions of optical fibers. Specifically, the receptacle is being configured to form a thermal communication when the vessels are loaded on the receptacle. Otherwise, the optical fibers have first and second end portions, wherein the first end portion and the second end portion of each optical fiber is being fixed with respect to each other for transmitting light emitted from the samples. By varying an in-ter-distance between the receptacle and the first end portions of the optical fibers, the vessels can be loaded to or unloaded from the receptacle to be brought in and out of thermal communication with the receptacle and light can be detected from the samples contained in the one or more receptacle-loaded vessels.

In some embodiments, the first end portions of the optical fibers are moved with respect to the receptacle while keeping the receptacle stationary. In some embodiments, the end portions of the optical fibers and the detection arrangement are commonly moved with respect to the receptacle while keeping the receptacle stationary.

According to a third aspect, a new device for determining a mapping between end portions of optical fibers in an instrument for thermally treating liquid samples is disclosed.

In some embodiments, the mapping device comprises a plate-like base configured to be put on a temperature-controlled receptacle for receiving a plurality of vessels for containing the liquid samples in thermal communication therewith. In some embodiments, the base is being provided with a plurality of light generating elements for generating light, wherein the light generating elements are being arranged in a manner to be optically coupled with a plurality of optical fibers configured for transmitting light emitted from the samples to at least one detector. In some embodiments, the mapping device comprises a controller set up for selectively supplying electric current to the light generating elements.

According to a fourth aspect, a new method for determining a mapping between end portions of optical fibers in an instrument for thermally treating liquid samples is disclosed.

In some embodiments, the method comprises a step of putting a plate-like base on a temperature-controlled receptacle for receiving a plurality of vessels for containing the samples in thermal communication therewith. In some embodiments, the method comprises a step of selectively supplying electric current to a plurality of light generating elements for generating light. In some embodiments, the method comprises a step of optically coupling the light into optical fibers configured for transmitting light emitted by the samples. In some embodiments, the method comprises a step of detecting the light exiting the optical fibers by at least one detector.

The above-described embodiments of the various aspects of the invention may be used alone or in any combination thereof without departing from the scope of the invention.

Various illustrated embodiments according to the present invention will be described in detail below with reference to the accompanying drawings, where like designations denote like or similar elements. First referring to FIGS. 1 through 10 embodiments of exemplary instruments for the automated thermal treating of liquid samples generally referred to at reference numeral 1 are explained. FIG. 1 illustrates various modules of the exemplary instruments depicted in FIGS. 2 to 10. Specifically, FIGS. 2 to 9 refer to a first exemplary instrument 1; FIG. 10 refers to a second exemplary instrument 1 only differing from the first one in the excitation and detection arrangements. In some embodiments, the instrument 1 is configured as a thermo-cycler for thermally cycling reaction mixtures of nucleic acids and one or more reagents through a series of temperature excursions and optically detecting the reaction products obtained. In some embodiments, the instrument 1 can be used to perform the PCR, in particular real-time PCR, or any other reaction of the nucleic acid amplification type. In some embodiments, the instrument 1 can be used for the optical on-line detection of reaction products. In some embodiments, the instrument 1 can be used for the isothermal treatment or execution of melting curves.

With particular reference to FIG. 1, in some embodiments, the instrument 1 includes various modules as detailed in the following description which are functional and (optionally) structural entities for treating liquid samples. Specifically, in some embodiments, the instrument 1 includes a thermal module 2 which can be brought in thermal communication with a multi-well plate 3 provided with plural vessels, cavities or wells 4 for receiving liquid samples 5. In some embodiments, the thermal module 2 can be heated or cooled according to pre-defined temperature profiles so as to transfer heat in controlled manner to/from the samples 5.

With continued reference to FIG. 1, in some embodiments, a detection module 6 can be used to detect light so as to identify reaction products which, in some embodiments, can be obtained as a result of a polymerase chain reaction of the samples 5. In some embodiments, the instrument 1 can be used for the optical on-line detection of the reaction products during progress of the amplification reactions.

As indicated by the double arrows, in some embodiments, the detection module 6 can at least vertically be moved in controlled manner relative to the thermal module 2 by means of a moving mechanism 52 (not further detailed in FIG. 1). In some embodiments, the moving mechanism 52 is an automated moving mechanism. The moving mechanism 52 can, e.g., be configured as driven rack and pinion mechanism or any other mechanism enabling at least a vertical movement of the detection module 6. Specifically, the moving mechanism 52 can, e.g., include a (controllable) driver such as, but not limited to, an electric motor or hydraulic actuator for automatically moving the detection module 6. Since those of skill in the art are aware of the specific configuration of such moving mechanism, it is not necessary to elucidate it further herein. Using the moving mechanism 52, in some embodiments, the detection module 6 can selectively be moved into a lowered first or operative position adapted for optically detecting reaction products obtained from the samples 5 or in a raised second or inoperative or loading/unloading position adapted for loading or unloading the instrument 1 with the multi-well plate 3.

With continued reference to FIG. 1, in some embodiments, the detection module 6 includes an excitation arrangement 7 provided with at least one light source 8 for generating excitation light 9 adapted to excite the emission of light 24 (e.g. fluorescence light), in the following denoted as "emitted light", by the samples 5. As illustrated, in some embodiments, the detection module 6 further includes a detection arrangement 10 provided with at least one detector 11 to optically detect the emitted light 24. In some embodiments, the detection module 6 further includes a coupling arrangement generally referred to at reference numeral 12 for optically coupling each of the excitation arrangement 7 and the detection arrangement 10 to the wells 4. Stated more particularly, in some embodiments, the coupling arrangement 12 includes plural first optical fibers 13, in the following denoted as "excitation fibers", for transmitting the excitation light 9 from the excitation arrangement 7 to the wells 4 and plural second optical fibers 14, in the following denoted as "emission fibers", for transmitting the emitted light 24 from the wells 4 to the detection arrangement 10. In some embodiments, each well 4 of the multi-well plate 3 is related to an individual pair of one excitation fiber 13 and one emission fiber 14.

As further illustrated in FIG. 1, in some embodiments, well-sided first end portions 15 of the excitation fibers 13 are fixed with respect to each other by means of a first fixing element 16, while second end portions 17 of the excitation fibers 13 opposite to the first end portions 15 thereof are fixed with respect to each other by a second fixing element 18. Otherwise, in some embodiments, well-sided first end portions 15 of the emission fibers 14 are fixed with respect to each other by means of the first fixing element 16, while second end portions 17 of the emission fibers 14 opposite to the first end portions 15 thereof are fixed with respect to each other by a third fixing element 19. Specifically, in some embodiments, the excitation light 9 can be coupled into the excitation fibers 13 at second end faces 61 and be coupled out of the excitation fibers 13 at first end faces 60 thereof. Otherwise, in some embodiments, the emitted light 24 can be coupled into the emission fibers 14 at first end faces 60 and be coupled out of the emission fibers 14 at second end faces 61.

With continued reference to FIG. 1, in some embodiments, an excitation optics generally referred to at reference numeral 20 is used to optically couple the excitation light 9 into the excitation fibers 13 at the second end faces 61. Specifically, in some embodiments, one or more excitation filters 22 are used for filtering one or more specific wavelengths or one or more ranges of wavelengths before the excitation light 9 is coupled into the excitation fibers 13. Otherwise, in some embodiments, in case the detection module 6 is in operative position, the first end faces 60 of the excitation fibers 13 are arranged in such a manner that the excitation light 9 is directed into the wells 4 to excite the emitted light 24 by the samples 5.

With continued reference to FIG. 1, in some embodiments, in case the detection module 6 is in operative position, the first end faces 60 of the emission fibers 14 are arranged in such a manner that the emitted light 24 can be coupled into the emission fibers 14. In some embodiments, an emission optics generally referred to at reference numeral 21 is used to optically couple the emitted light 24 leaving the emission fibers 14 at the second end faces 61 to the detector 11. In some embodiments, one or more emission filters 23 are used for filtering one or more wavelengths or one or more ranges of wavelengths from the emitted light 24 before the emitted light 24 hits the detector 11.

In the instrument 1, in some embodiments, one pair of optical fibers 13, 14 is used as optical reference channel for performing reference measurements. Instead of a normal sample one or a set of reference samples can be contained in a well 4 associated with the optical fibers 13, 14. In some embodiments, the reference samples are made of fluorescent glass or crystal such as, but not limited to, terbium glass or ruby.

With continued reference to FIG. 1, in some embodiments, the instrument 1 has an implemented (dedicated) reference channel 116 configured to monitor brightness and intensity of the light source 8 generating the excitation light 9. The signal of the reference channel 116 can be used to survey the light source 8 and/or to control the intensity of the excitation light 9 so as to have a constant intensity, e.g., by means of a feedback regulation loop. Alternatively the signal of the reference channel 116 can be used to normalize the measured sample fluorescence data. The reference channel 116 consists of one reference channel fiber 117 configured to direct light generated by the light source 8 to a reference channel detector 118 for measuring the intensity of light transmitted through the reference channel fiber 117. In some embodiments, the reference channel detector 118 is being connected to an electronic amplifier (not illustrated) and an analogue digital converter (not illustrated).

In some embodiments, the controller 25 for controlling the automated thermal treating of the samples 5 is configured as microcontroller running a computer-readable program provided with instructions to perform operations in accordance with a pre-defined sequence of steps. Specifically, the controller 25 receives in-formation from the various components of the instrument 1, especially from the detector 11, and generates and transmits corresponding control signals to the components which require control such as the moving mechanism 52 for vertically moving the detection module 6, the light source 8 and the thermal module 2. As schematically illustrated in FIG. 1, in some embodiments, electric lines 26 are used for transmitting the electric signals.

Figure 5:
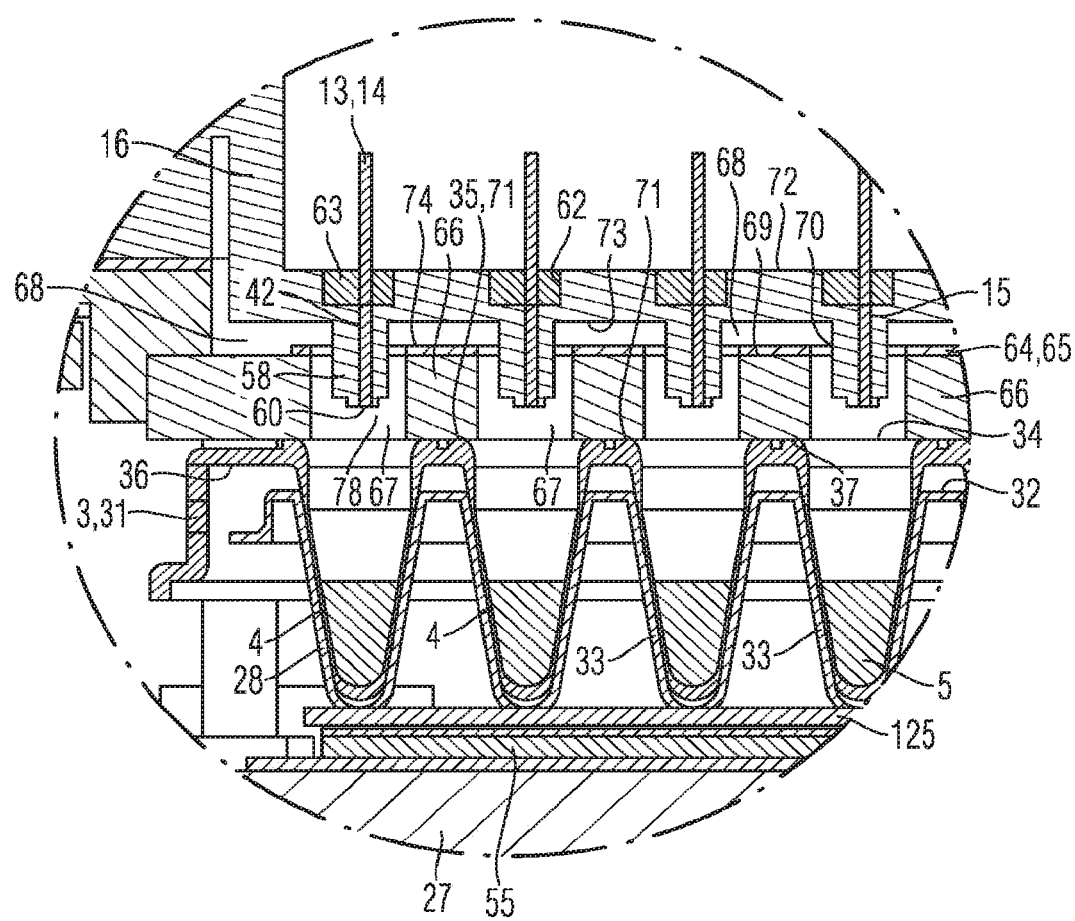
FIG. 5 illustrates another enlarged detail of the instrument of FIGS. 2 to 3 according to circle A of FIG. 4.

With particular reference to FIGS. 2 to 10, exemplary embodiments of the instrument 1 as schematically illustrated in FIG. 1 now are explained. Specifically, FIGS. 2 to 9 refer to a first variant of the exemplary instrument 1, while FIG. 10 refers to a second variant thereof. Accordingly, in some embodiments, the thermal module 2 includes a temperature-controlled (thermal) block 27 made of material having good thermal conductivity such as metallic material. As illustrated in FIG. 5, in some embodiments, the thermal block 27 is provided with one or more thermoelectric devices 55 which, in some embodiments, utilize the Peltier effect. Connected to a DC power source (not illustrated), each of the thermoelectric devices 55 functions as heat pump for producing or absorbing heat depending upon the direction of the electric current applied. In some alternative embodiments, the thermoelectric devices 55 are replaced by other heating devices such as resistive heaters which can be heated based on Ohmic heating in combination with cooling means such as a fan for cooling the thermal block 27 with air. In some alternative embodiments, the thermal block 27 is provided with channels which can be flown-through by liquids having different temperatures. Generally other heating/cooling means as known from the prior art may be used.

In some embodiments, on an upper side thereof, the thermal block 27 is integrally formed with a plate-like receptacle 28 adapted for holding the multi-well plate 3 in thermal communication with the thermal block 27 and, in some embodiments, is made of material having good thermal conductivity so as to enable heat transfer to/from the samples 5 contained in the wells 4. In some embodiments, the thermal module 2 includes a heat exchanger 29 thermally coupled to the thermal block 27 on a lower side thereof. Specifically, in some embodiments, the heat exchanger 29 is provided with plural plate-like ribs 30 serially arranged with respect to each other keeping a small in-ter-distance to enable effective heat transfer to the ambient.

In some embodiments, the thermoelectric devices 55 of the thermal module 2 can be supplied with electric current to heat or cool the receptacle 28 so as to change and hold various temperatures of the samples 5 for a predetermined amount of time under control of the controller 25. Specifically, in some embodiments, the controller 25 can transmit control signals to the thermoelectric devices 55 to regulate the desired temperature of the receptacle 28 which, in some embodiments, is varied in response to the input of a temperature sensor (not illustrated) for sensing the temperature of the receptacle 28 and/or the samples 5.

As illustrated in FIG. 5, in some embodiments, an upper face 32 of the receptacle 28, in the following denoted as "upper receptacle face" is provided with plural recesses 33, the inner profiles of which are conform in shape with the outer contours of the wells 4 at least in their lower parts so that the multi-well plate 3 can be placed upon the receptacle 28 in a position where the wells 4 rest inside the recesses 33. Accordingly, due to an at least partially close fit, good thermal communication between the receptacle 28 and the wells 4 can be obtained resulting in a highly efficient transfer of heat between the receptacle 28 and the wells 4. Otherwise, in some embodiments, a lower face 36 of the multi-well plate 3, in the following denoted as "lower plate face" is distanced from the upper receptacle face 32 in regions in-between the wells 4 to improve the thermal transfer between the receptacle 28 and the wells 4.

In some embodiments, the multi-well plate 3 comprises a main base 31 having an upper face 35, in the following denoted as "upper plate face", which is provided with a rectangular array of wells 4 for receiving the samples 5. The array may, e.g., include 8×12 wells (96 wells), 6×10 wells (60 wells), 16×24 wells (384 wells), or any other number and arrangement that would be compatible with the automated instrument 1 for thermally treating the samples 5. The footprint of the multi-well plate 3 may, e.g., be about 127 mm in length and about 85 mm in width, while those of skill in the art will recognize that the multi-well plate 3 can be formed in dimensions other than those specified herein. In some embodiments, the multi-well plate 3 consists of plastic material such as but not limited to polypropylene, polystyrene and polyethylene. In some embodiments, the multi-well plate 3 is intended for single use only so that it can be filled with samples 5 for a single experiment and is thereafter discarded.

In some embodiments, a transparent sealing cover 34 is fixed to the upper plate face 35 at planar contact regions 71 thereof located in-between the wells 4 by adhesion or thermal sealing. Specifically, the transparent sealing cover 34 air-tightly seals the open-top wells 4 in order to prevent evaporation of the samples 5 and to shield the samples 5 from external influences such as cross-contamination. In some embodiments, the transparent sealing cover 34 is made of an optically transparent material such as a clear film exhibiting low fluorescence when exposed to the excitation light 9. In some embodiments, the transparent sealing cover 34 is made of one or more polymers selected from the group consisting of poly-styrene, polyethylene and polyester. In some embodiments, the transparent sealing cover 34 is a multi-layered film, e.g., consisting of one layer of polypropylene and one layer of polyester. In some embodiments, the transparent sealing cover 34 comprises one or more compliant coatings and/or one or more adhesives such as a pressure sensitive adhesive or a hot melt adhesive for fixing the transparent sealing cover 34 to the upper plate face 35. The transparent sealing cover 34 allows for an optical detection of the emitted light 24, e.g., during progress of the polymerase chain reaction so as to enable an optical on-line detection of the reaction products obtained. The transparent sealing cover 34 thus allows the excitation light 9 to be transmitted to the wells 4 and the emitted light 24 to be transmitted back to the one or more detectors 11. In some embodiments, the sealing cover 34 is applied to the multi-well plate 3 after the samples have been filled into the wells 4 and before the multi-well plate 3 is loaded in the instrument 1.

Figure 2:
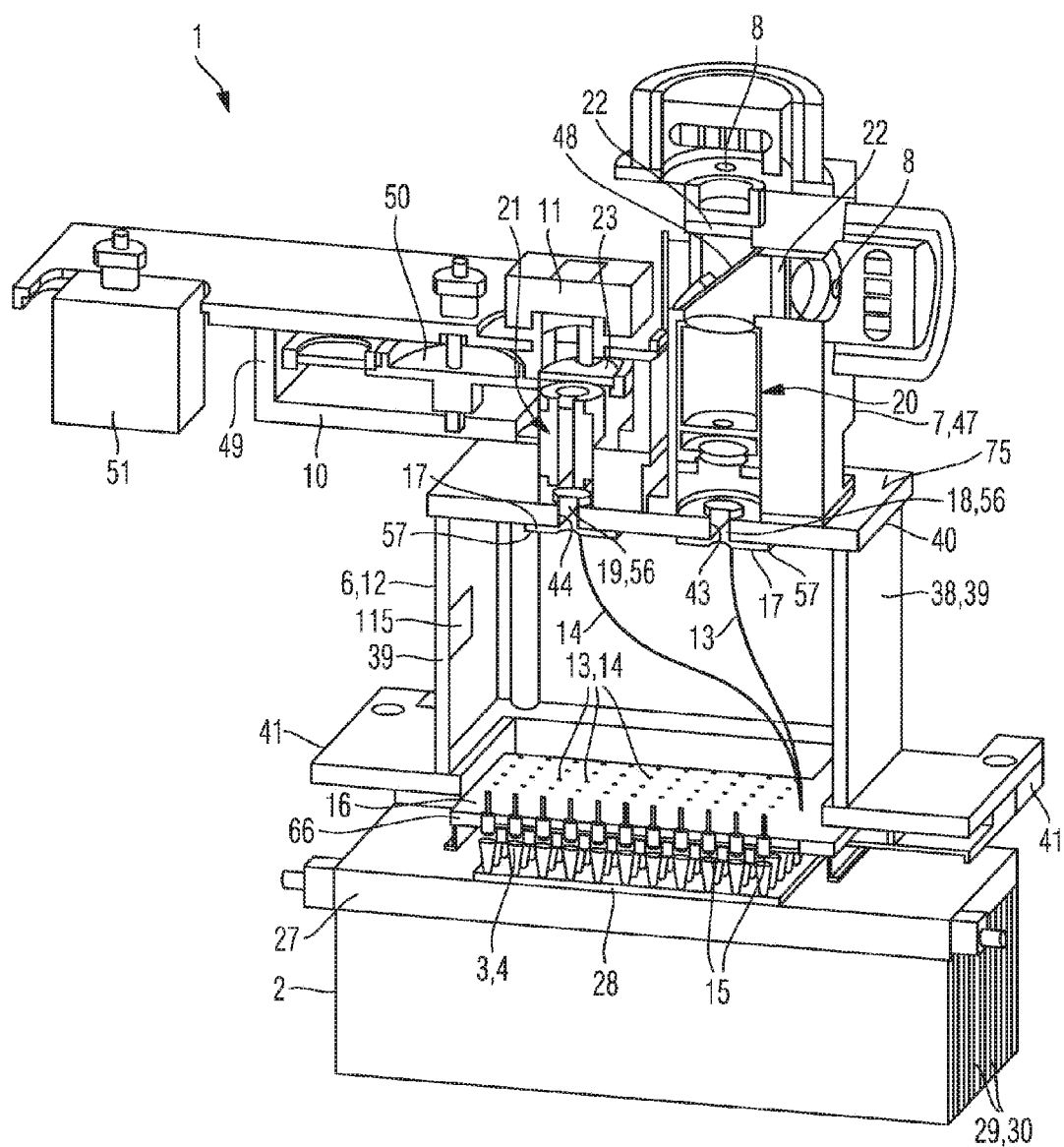
FIG. 2 is a partly sectioned perspective view of an exemplary instrument the modules of which are schematically illustrated in FIG. 1.

With particular reference to FIG. 2, in some embodiments, the coupling arrangement 12 comprises a rigid chassis 38 including four vertical plates 39, a upper horizontal plate 40 and two spaced-apart lower horizontal plates 41 assembled by conventional fixation means such as screws, bolts or welded connections. In some embodiments, the first fixing element 16 for fixing the first end portions 15 of both the excitation and emission fibers 13, 14 is a rectangular solid plate fixed to the lower horizontal plates 41 so as to be integrally formed with the chassis 38. In some embodiments, each of the second and third fixing elements 18, 19 for fixing the second end portions 17 of the emission and excitation fibers 13, 14, respectively, comprises a cylindrical portion 56 and a disk-like planar portion 57. As illustrated, in some embodiments, the cylindrical portions 56 are inserted into first and second openings 43, 44, respectively, formed by the upper horizontal plate 40 and are fixed therein like plugs. Fixed to the upper horizontal plate 40, the second and third fixing elements 18, 19 are integrally formed with the chassis 38.

As, e.g., illustrated in FIG. 5, in some embodiments, the first fixing element 16 is provided with an array of first through-holes 42. In some embodiments, the number and arrangement of the first through-holes 42 correspond to the number and arrangement of the wells 4 wherein the first through-holes 42 can, e.g., be located right above the wells 4. With continued reference to FIG. 5, in some embodiments, each first through-hole 42 accommodates the first end portions 15 of a pair of one excitation fiber 13 and one emission fiber 14 allowing the excitation light 9 transmitted by the excitation fibers 13 to be directed into the wells 4 for irradiating the samples 5. Otherwise, the emitted light 24 can be received by the emission fibers 14. In some alternative embodiments, two first through-holes 42 are provided for each well 4, one for accommodating the first end portion 15 of the excitation fiber 13 and the other one for accommodating the first end portion 15 of the emission fiber 14, so that each first end portion 15 is accommodated in a separate first through-hole 42. In some embodiments, the two first through-holes 42 related to one well 4 are spaced apart to have a distance from each other in a range of from 0.1 to 2 mm. Those of skill in the art will recognize that inter-distances other than those specified herein can be envisaged according to the specific demands of the user.

Figure 8:
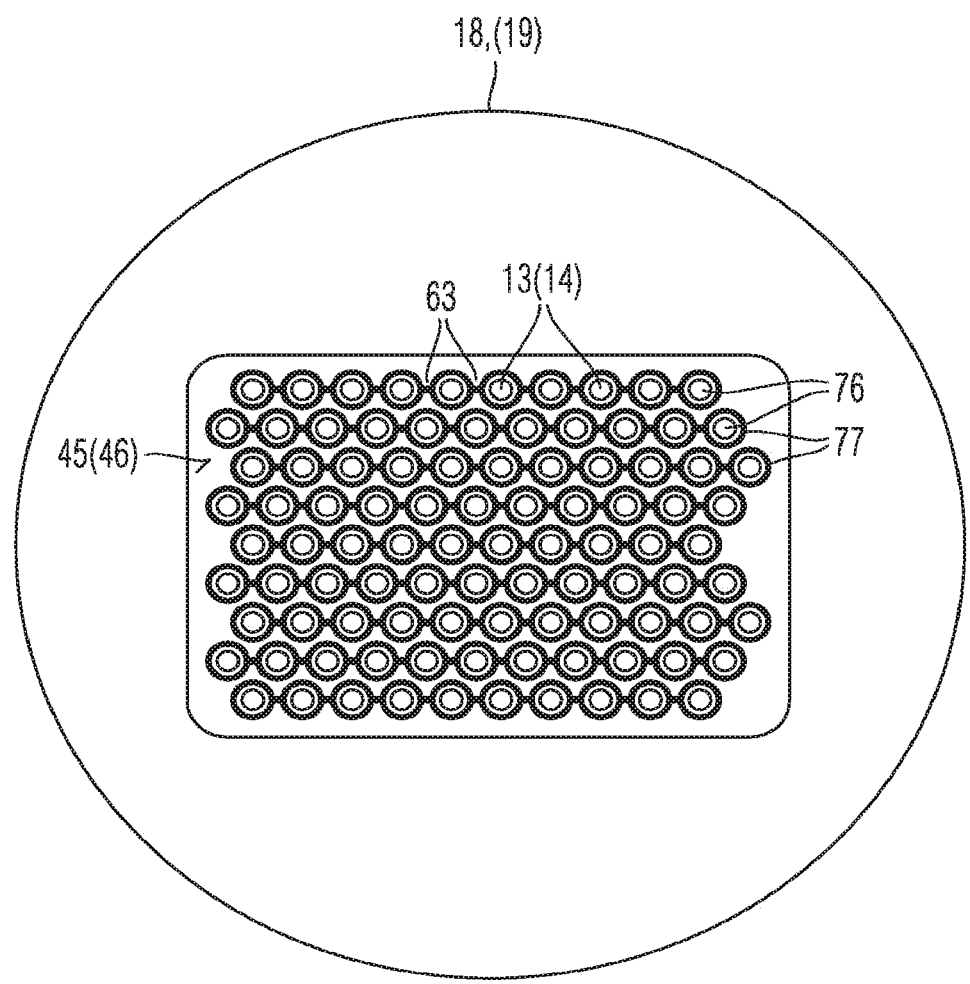
FIG. 8 illustrates a fixing element for fixing the second end portions of the optical fibers of the instrument of FIGS. 2 to 7.

With particular reference to FIG. 8 illustrating one of the second or third fixing elements 18, 19, in some embodiments, the second fixing element 18 is provided with one second through-hole 45 and the third fixing element 19 is provided with one third through-hole 46, wherein the second through-hole 45 accommodates all second end portions 17 of the excitation fibers 13 and the third through-hole 46 accommodates all second end portions 17 of the emission fibers 14. Specifically, while FIG. 8 depicts the second fixing element 18, the third fixing element 19 is similar in construction as indicated by the reference signs in brackets related to the third fixing element 19. As illustrated, in some embodiments, the excitation fibers 13 and the emission fibers 14, respectively, are fixed with respect to each other and with the corresponding through-hole 45, 46 by an adhesive material 63 and may be randomly arranged. In some alternative embodiments, instead of one second through-hole 45 accommodating the second end portions 17 of the excitation fibers 13 and one third through-hole 46 accommodating the second end portions 17 of the emission fibers 14, the second and third fixing elements 18, 19 can respectively be provided with one through-hole (not illustrated) accommodating all second end portions 17 of both the excitation and emission fibers 13, 14, wherein in some embodiments, the second end portions of both the excitation and emission fibers 13, 14 are fixed with respect to each other by an adhesive material. In some yet alternative embodiments, instead of one second through-hole 45 accommodating the second end portions 17 of the excitation fibers 13 and one third through-hole 46 accommodating the second end portions 17 of the emission fibers 14, the second and third fixing elements 18, 19 can respectively be provided with an array of first and second through-holes 45, 46. Stated more particularly, the second fixing element 18 can be provided with an array of second through-holes 45 accommodating the second end portions 17 of the excitation fibers 13, wherein each second through-hole 45 accommodates the second end portion 17 of one excitation fiber 13, and the third fixing element 19 can be provided with an array of third through-holes 46 accommodating the second end portions 17 of the emission fibers 14, wherein each third through-hole 46 accommodates the second end portion 17 of one emission fiber 14. Accordingly, in the coupling arrangement 12 there is a fixed one-to-one relationship or mapping between the first end face 60 of the fixed first end portion 15 and the second end face 61 of the fixed second end portion 17 of individual optical fibers 13, 14. Otherwise, in operative position of the detection module 6 allowing light to be transmitted between the wells 4 and the optical fibers 13, 14, a one-to-one relationship or mapping between the wells 4 and the second end faces 61 of the fibers 13, 14 is given. Due to the mapping, light can selectively be transmitted to each of the wells 4 and/or selectively received therefrom by coupling the excitation light 9 into specific second end faces 61 of the excitation fibers 13 and coupling the emitted light 24 out of specific second end faces 61 of the emission fibers 14.

Figure 6:
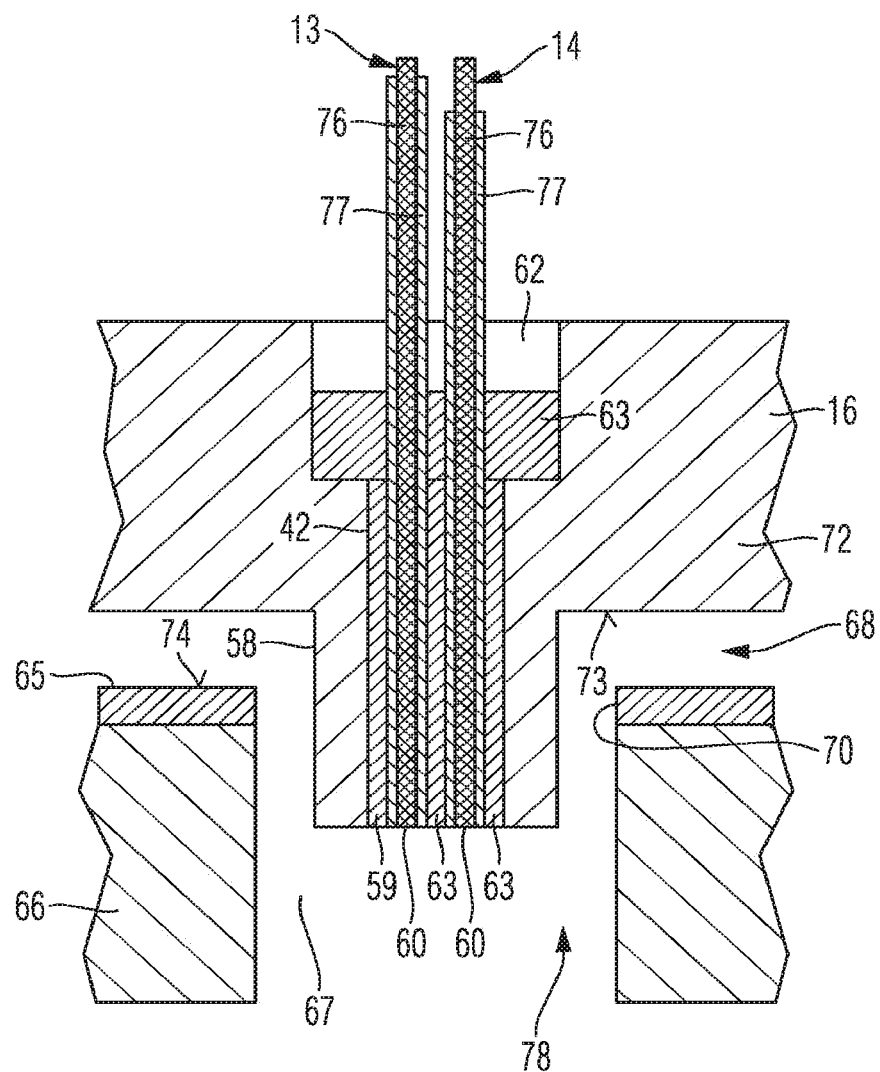
FIG. 6 illustrates another enlarged detail of the instrument of FIGS. 2 to 5.

As illustrated in FIGS. 5 and 6 depicting enlarged detailed views of the instrument 1, in some embodiments, the first fixing element 16 is provided with a plate-like planar portion 72 provided with projections 58 projecting towards the multi-well plate 3. In one embodiment, the projections 58 are cylindrical in shape, and in other embodiments the projections 58 may be rectangular or square in their cross-sectional shape. In still other embodiments, other shapes may be used to define the cross-sectional shape of the projections 58 so long as the projections are sized to fit into the plate holes 67. Specifically, in some embodiments, each of the first through-holes 42 penetrates the planar portion 72 and accommodates one projection 58 in a centered position. Stated more particularly, in some embodiments, one first through-hole 42 accommodates the first end portions 15 of one pair of one excitation fiber 13 and one emission fiber 14 wherein the first end faces 60 thereof are flush with an orifice 59 of the first through-hole 42. In one embodiment orifice 59 may be circular in cross-section and in other embodiments may have any other suitably shape in cross-section so long as the pair of one excitation fiber 13 and one emission fiber 14 is accommodated therein. Moreover, in some embodiments, each of the first through-holes 42 is provided with a ring-like broadened hollow 62 adjacent to an upper side of the first fixing element 16 filled with adhesive material 63 in order to fix the first end portions 15 of the optical fibers 13, 14 accommodated therein. While only one optical fiber 13, 14 per first through-hole 42 is shown in FIG. 5, it is to be understood, that, in some embodiments, each first through-hole 42 accommodates one excitation fiber 13 and one emission fiber 14 as depicted in FIG. 6. Similarly, the second end portions 17 of the optical fibers 13, 14 are fixed to the second and third fixing elements 18, 19, respectively, by an adhesive material which is not further detailed in the figures. Accordingly, the optical fibers 13, 14 are not fixed in regions other than the fixed first and second end portions 15, 17. In some alternative embodiments (not illustrated), the optical fibers 13, 14 are fixed in-between the first and second end portions 15, 17, e.g., by means of an adhesive such as, but not limited to a polyurethane foam, in order to reduce the motility of the optical fibers 13, 14.

Due to the fact that at least the first and second end portions 15, 17 of the optical fibers 13, 14 are fixed with respect to each other, it can be avoided that mechanical forces act on the optical fibers 13, 14 during a vertical movement of the detection module 6. Accordingly, changes of the shape of the optical fibers 13, 14 (fiber bending) which usually go along with undesired variations of the optical properties of the optical fibers 13, 14 can be avoided. Hence, the reliability and reproducibility of the detection results are improved. Otherwise, lifetime of the optical fibers 13, 14 can be prolonged.

As illustrated in FIG. 6, in some embodiments, each of the excitation and emission fibers 13, 14 is comprised of a core 76 made of optically transparent material such as, but not limited to fused silica or a plastic polymer. In some embodiments, the core 76 is coated by a cladding (not illustrated) made of material having a lower optical refraction index than the core 76 so as to keep light within the core 76. As illustrated, in some embodiments, the optical fibers 13, 14 are provided with an opaque coating 77 permitting the fibers 13, 14 to be readily stick together without removing the coating 77 facilitating production of the instrument 1. In some embodiments, the cores 76 have a diameter in the range of from 0.05 mm to 1.5 mm, preferably 0.1 to 0.8 mm. In some embodiments, the optical fibers 13, 14 including the coatings 77 have a diameter in the range of from 0.3 to 2 mm, preferably 0.4 mm to 1.0 mm.

Specifically, when performing the PCR, it is desirable that the samples 5 have temperatures throughout the thermo-cycling process that are as uniform as reasonably possible since even small variations can cause a failure or undesirable outcome of the amplification process. Otherwise, since the wells 4 usually are not completely filled with samples 5, air gaps can be present in the wells 4 between the liquid samples 5 and the sealing cover 34. Hence, thermo-cycling can cause formation of condensates on the underside of the sealing cover 34 which reduces the optical transmission of the sealing cover 34 and thus may interfere with the optical detection of the emitted light 24. Condensates otherwise are likely to vary the composition of the reaction mixtures.

With continued reference to FIGS. 5 and 6, in order to overcome such drawbacks, in some embodiments, the coupling arrangement 12 includes a cover heater 64 for heating the sealing cover 34 fixed to the lower horizontal plates 41 of the chassis 38 in a manner to be in good thermal contact therewith. Specifically, in some embodiments, the cover heater 64 includes a heating plate 66 made of material having good thermal conductivity such as metallic material, e.g., stainless steel or aluminum. The heating plate 66 has a lower contact face 37 which in operative position of the detection module 6 contacts the sealing cover 34. In some embodiments, the heating plate 66 has a thickness in a range of from 2 to 7 mm. In some embodiments, the heating plate 66 has a thermal conductivity of more than 5 W/m/K.

As illustrated, in some embodiments, the cover heater 64 further includes a heating element 65 for generating heat attached to an upper plate face 69 of the heating plate 66. In some embodiments, the heating element 65 is adapted to generate Ohmic heating and, e.g., can be provided with resistive heating lines (not illustrated).

With continued reference to FIG. 5, in some embodiments, the heating plate 66 is provided with a plurality of plate holes 67 the number and arrangement of which correspond to the wells 4 of the multi-well plate 3. As illustrated, in some embodiments, in operative position of the detection module 6, the contact face 37 contacts the sealing cover 34 only in contact regions 71 in-between adjacent wells 4. Specifically, in some embodiments, a mechanical pressure can be exerted on the contact regions 71 by means of the contact face 37 to press the wells 4 into the recesses 33 of the receptacle 28 so as to obtain a reliable thermal contact between the multi-well plate 3 and the thermal block 27. In general, the cover heater 64 enables minimization of temperature errors and variations between the samples 5, in particular, by reducing edge effects which may cause temperature differences between outer and inner wells 4. Otherwise, formation of condensate on the sealing cover 34 can be avoided.

In some embodiments, the controller 25 is electrically connected to the cover heater 64 by electric lines (not illustrated) to regulate a desired thermal output which, in some embodiments, is being varied in response to the input from one or more temperature sensors (not illustrated) for sensing the temperature of the heating plate 66. In some embodiments, it can be preferred to regulate the thermal output in a manner that the temperature of the heating plate 66 is 5° C. to 15° C. above a maximum temperature of the reaction mixture which in case of the polymerase chain reaction may, e.g., be in a range of from 95° C. to 110° C.

With continued reference to FIGS. 5 and 6, in some embodiments, the heating element 65 is provided with a plurality of element holes 70, each of which opens into the plate holes 67 to thereby form common cover heater holes 78. As illustrated in FIG. 6, in some embodiments, the element holes 70 are flush with the plate holes 67. In some embodiments, the cover heater holes 78 are configured as cylindrical through-holes. In some embodiments, each of the projections 58 accommodating the optical fibers 13, 14 steps into a separate cover heater hole 78 without being in direct contact with the cover heater 64 so as to avoid conductive heat transfer to the optical fibers 13, 14.

In some embodiments, in operative condition of the detection module 6, that is to say, in a position where the contact face 37 contacts the contact regions 71 in-between the wells 4, the cover heater holes 78 form closed cavities avoiding convecting air so as to improve uniformity of the temperature of the samples 5. Otherwise, in some embodiments, plural air-filled cavities 68 are formed between a lower planar portion face 73 of the planar portion 72 of the first fixing element 16 and an upper heating element face 74 of the heating element 65. Accordingly, thermal communication between the first fixing element 16, in particular the optical fibers 13, 14 fixed therein, and the cover heater 64 can be reduced.

In some embodiments, the cover heater holes 78 and/or the cavities 68 above the cover heater 64 are at least partly filled with material having poor thermal conductivity such as plastic material so as to reduce thermal coupling between the optical fibers 13, 14 and the cover heater 64. In some embodiments, the optical fibers 13, 14 are coated by or embedded in material having poor thermal conductivity such as plastic material so as to reduce thermal coupling between the optical fibers 13, 14 and the cover heater 64 and to prevent any even small distortion of the material when operating the detection module 6. In some embodiments, the material having poor thermal conductivity is used to fix the optical fibers 13, 14 within the first through-holes 42.

The fixation of the optical fibers 13, 14 and sometimes the optical fibers 13, 14 themselves depending on their material are sensitive to heat. Due to the fact that the optical fibers 13, 14 are largely thermally de-coupled from the cover heater 64 as above-detailed, lifetime of the optical fibers 13, 14 and their fixation can be prolonged. Similarly, thermal de-coupling of the excitation and emission optics 20, 21 from the cover heater 64 can also be reached. Another feature is given by the fact that each well 4 optically communicates with only one cover heater hole 78 in such a manner that the wells 4 are optically shielded with respect to each other.

Figure 3:
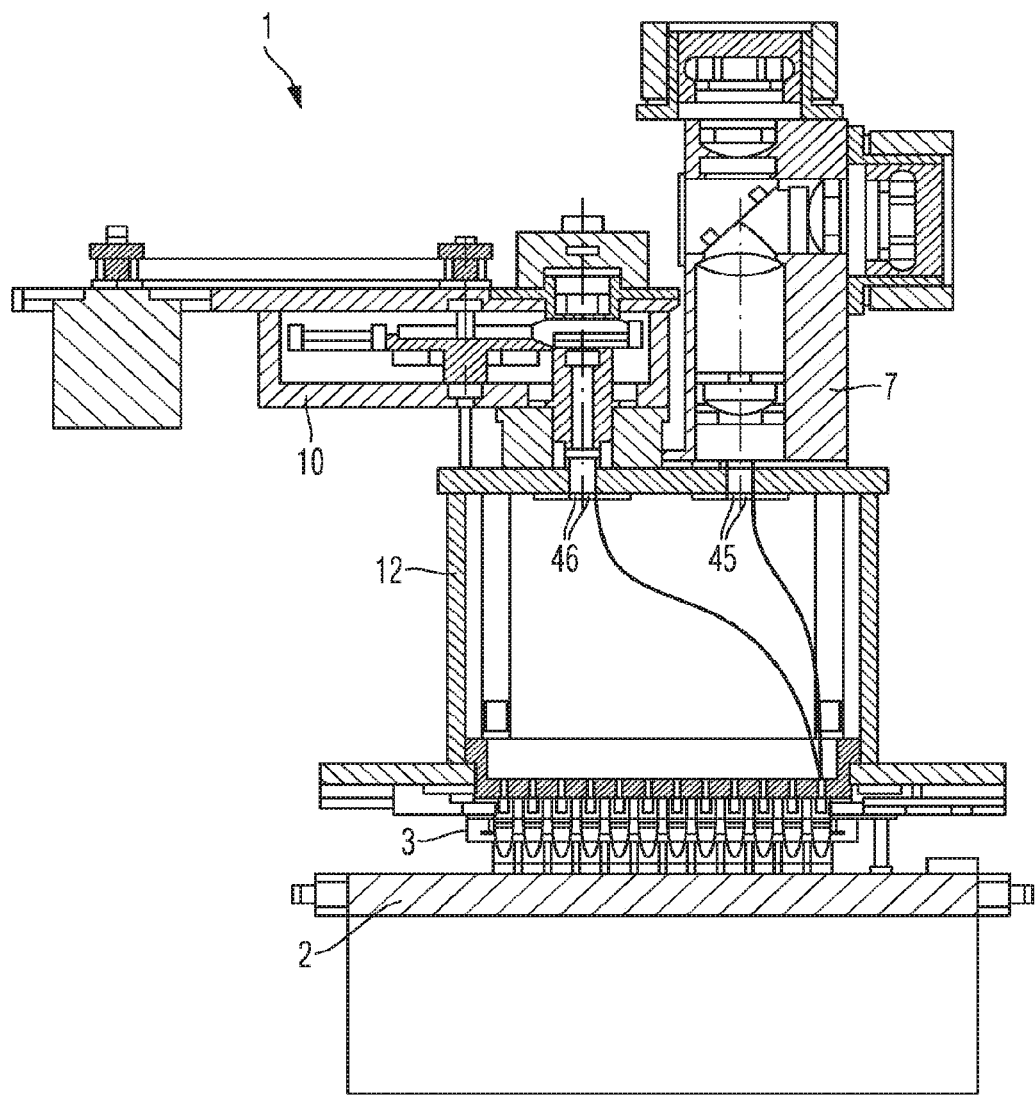
FIG. 3 is a sectional view of the instrument of FIG. 2.
Figure 4:
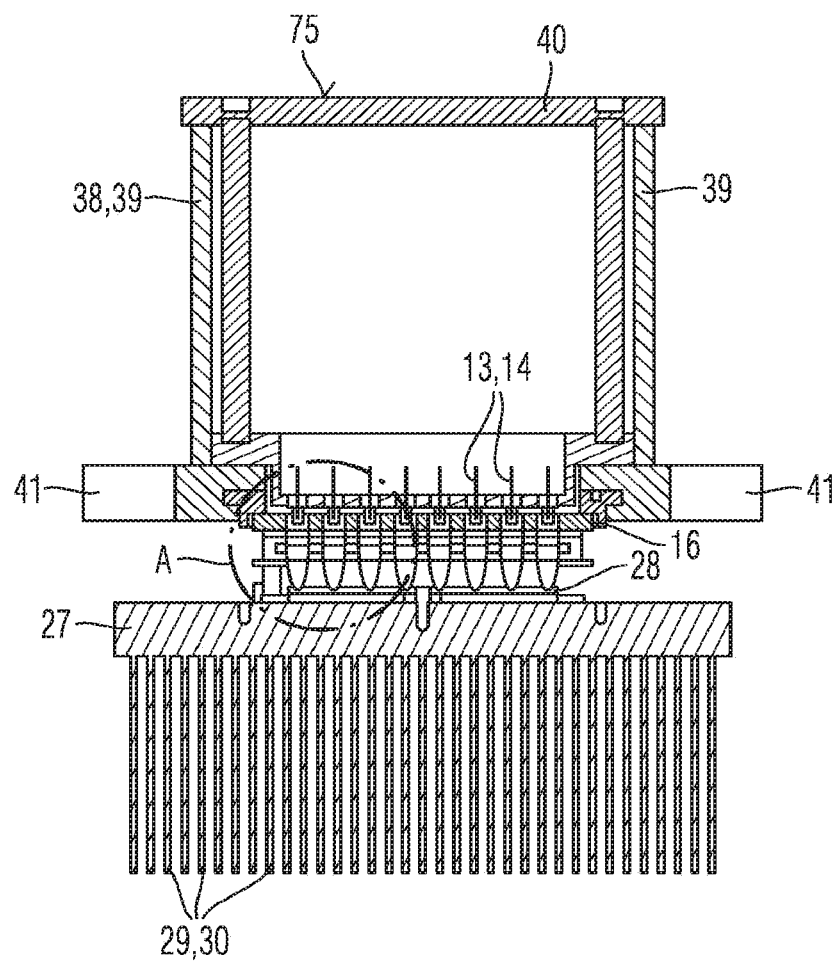
FIG. 4 illustrates an enlarged detail of the instrument of FIGS. 2 to 3.

With continued reference to FIGS. 2 and 3, in some embodiments, the excitation arrangement 7 is accommodated in a first casing 47 which being fixed to an upper face of the upper horizontal plate 40, in the following denoted as "upper horizontal plate face 75", is integrally formed with the chassis 38. The purpose of the excitation arrangement 7 is to direct excitation light into the excitation fibers 13. Those of skill in the art will appreciate that wavelength, power, homogeneity and aperture are subject to the design chosen according to the specific demands of the user.

As illustrated in FIG. 2, in some embodiments, the ex-citation arrangement 7 includes two light sources 8 such as, but not limited to, light emitting diodes (LEDs) having two different wavelengths. The light sources 8 are arranged in orthogonal relationship with respect to each other, wherein each light source 8 is optically coupled to one or more excitation filters 22 for filtering the excitation light 9 incident on a dichroic mirror 48. In some embodiments, the optics, e.g., is designed to generate a homogeneous illuminated spot having a diameter of 8 mm and a numerical aperture of 0.15 in order to direct light into the excitation fibers 13. In some embodiments, two or more LEDs are coupled by dichroic mirrors and/or by fiber optics and/or by moving or rotating elements such as moving or rotating mirrors or prisms in order to direct the light to an excitation adapter. The use of multiple colored LEDs is useful for high excitation power. In order to measure the fluorescence with various excitation wavelength ranges the LEDs can be switched or the rotating elements can be rotated. In some embodiments, a white light source such as a halogen lamp or a white LED is used in combination with a filter wheel or filter sledge (as illustrated in FIG. 1). In some embodiments, the detection arrangement 10 is accommodated in a second casing 49 which being fixed to the upper horizontal plate face 75 is integrally formed with the chassis 38. The purpose of the detection arrangement 10 is to measure the emitted light 24 exiting the emission fibers 14.

As illustrated, in some embodiments, the detection arrangement 10 includes plural detectors 11, each of which having one light-sensitive element or at least one detector 11 having a plurality of light-sensitive elements for optically detecting the emitted light 24 such as, but not limited to, laterally resolving detectors like charge coupled detectors (CCDs) and CMOS detectors, and linear array detectors which can be moved for scanning and two-dimensional-array sensors such camera sensors. The emission optics 21 is used to transmit the emitted light 24 towards the detector 11 which, in some embodiments, is optically coupled to one of a plurality of emission filters 23 for filtering the emitted light 24.

With continued reference to FIG. 2, in some embodiments, plural emission filters 23 are attached to a filter wheel 50 which can be spun around a central spin axis by means of electric motor 51 so as to selectively move one emission filter 23 into the optical path of the emitted light 24. In some embodiments, the emitted light 24 is directed to multiple detectors such as CCD-cameras in parallel, e.g., after the emitted light 24 has been chromatically separated by dichroic mirrors and/or conventional filters. Stated more particularly, in some embodiments, a picture of the second end faces 61 of the second end portions 17 of the emission fibers 14 is obtained by the detectors 11 without having a one-to-one mapping between the second end faces 61 and the pixels of the detectors 11. Instead, the picture is processed to determine the light intensity from each fiber. Based on the one-to-one mapping information of the first and second end portions 15, 17 of the emission fibers 14, the determined light intensity can be attributed to a particular vessel. In some alternative embodiments, a plurality of detectors 11 can be assigned to the second end faces 61 of the emission fibers 14 in a one-to-one relationship so that each second end face 61 is related to one assigned detector 11.

In some embodiments, the excitation and emission optics 20, 21 include one or more light guiding and/or light shaping and/or light directing elements (not illustrated) such as, but not limited to, lenses and planar or bent mirrors and/or one or more light separating elements (not illustrated) such as, but not limited to, transmission gratings, reflective gratings and prisms in order to transmit the excitation light 9 to the samples 5 and to detect the emitted light 24 by the plurality of detectors 11. For this purpose, in some embodiments, the controller 25 is operatively coupled to the light sources 8 and the detectors 11 to output control signals for emitting the excitation light 9 and detecting the emitted light 24. Otherwise, the excitation and emission filters 22, 23 can be changed according to the specific demands of the user.

Figure 7A:
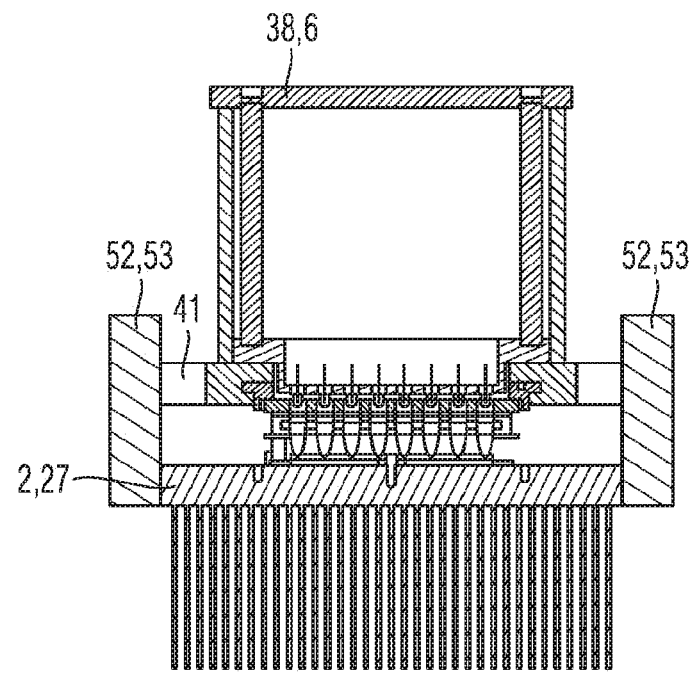
FIGS. 7A-7B are sectional partial views of the instrument of FIGS. 2 to 6 illustrating a vertical movement of the detection module.
Figure 7B:
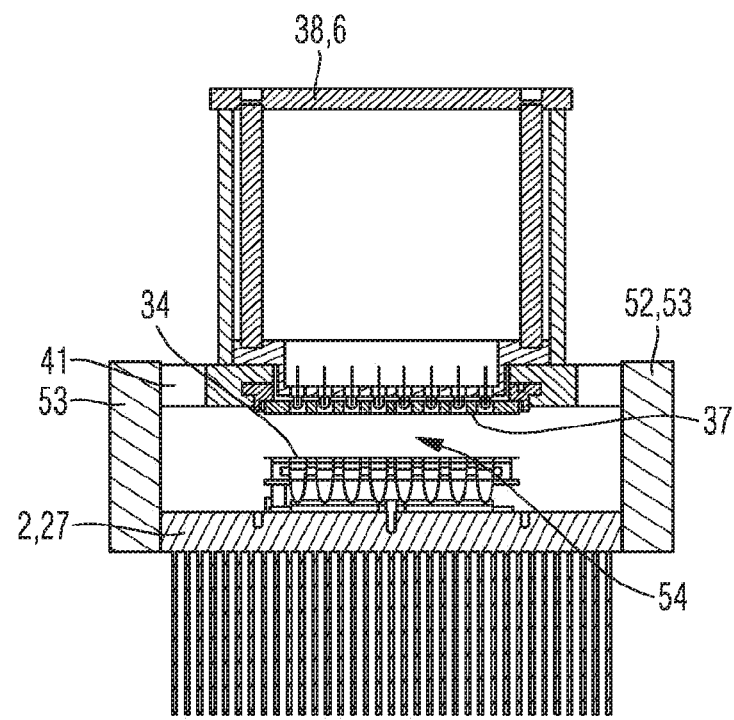

With particular reference to FIGS. 7A and 7B, in some embodiments, the instrument 1 includes an automated moving mechanism 52 allowing the detection module 6 to be at least vertically moved relative to the thermal module 2. In some embodiments, the detection module 6 can be moved vertically and horizontally. As illustrated, in some embodiments, the moving mechanism 52 includes two vertical guiding rails 53 which are fixed to the thermal block 27 in guiding engagement with the two lower horizontal plates 41 of the chassis 38 for linearly guiding the detection module 6. In some embodiments, the moving mechanism 52 further includes an actuating mechanism such as, but not limited to, a spindle drive operatively coupled to the chassis 38 for moving the detection module 6 relative to the thermal module 2 along the guiding rails 53. Hence, the detection module 6 can at least vertically be moved towards and away from the thermal module 2. As illustrated in FIG. 7A, in some embodiments, the detection module 6 can vertically be lowered into operative position for thermally treating the samples 5 and, as illustrated in FIG. 7B, vertically raised into inoperative position in which the detection module 6 is distanced from the thermal module 2. Specifically, in inoperative position, a free space 54 is created in-between the detection module 6 and the thermal module 2 allowing the multi-well plate 3 to be brought in a position on the thermal block 27 for thermally treating the samples 5. In some embodiments, the multi-well plate 3 can be manually placed on the thermal block 27 or removed therefrom. Those of skill in the art will recognize that the vertical dimensions of the free space 54 can be varied according to the specific demands of the user.

On the other hand, in some embodiments, the moving mechanism 52 is adapted to forcibly press the detection module 6 on the thermal module 2, that is to say, to apply a desired pressure force on the multi-well plate 3. Accordingly, the wells 4 can be pressed into the recesses 33 of the receptacle 28 by means of the contact face 37 with a view of improving the thermal communication between the multi-well plate 3 and the thermal block 27 so as to make the heat distribution uniform. Otherwise, the pressure force can improve the sealing effect of the transparent sealing cover 34. In some embodiments, the detection module 6 can be manually pressed on the multi-well plate 3. In some embodiments, the detection module 6 can be automatically pressed on the multi-well plate 3. For this purpose, in some embodiments, the controller 25 is electrically connected to the moving mechanism 52 to output control signals to regulate the automated vertical movement of the detection module 6. In some embodiments, the pressure force exerted on the multi-well plate 3 is in a range of from 100 N to 1000 N, preferably in a range of from 200 N to 600 N. Otherwise, in some embodiments, the detection module 6 can be manually raised in inoperative position to generate the free space 54 for the manual and/or automated charging or uncharging of the instrument 1 with the multi-well plate 3.

With particular reference to FIGS. 9A to 9F, in some embodiments, the thermal module 2 can be moved out in a charging/uncharging position outside an instrument casing 90 for charging the multi-well plate 3 on the receptacle 28 and removing it therefrom, respectively, or in a processing position inside the instrument casing 90 for thermally treating the liquid samples 5 and detecting the reaction products obtained by means of the detection arrangement 10, e.g., provided by detection module 6. Stated more particularly, the instrument 1 includes a horizontally movable tray 102 comprising a horizontal supporting base 103 supporting the thermal module 2 and a vertical front cover 105 mounted to the supporting base 103 for closing the instrument casing 90 in processing position of the thermal module 2. The supporting base 103 comprises one or two parallel beams 104 slidably engaged with horizontal guiding rails 113 vertically fixed to a base 89 of the instrument 1 allowing the tray 102 to be slidably moved in and out of the instrument casing 90.

The instrument 1 further includes a bi-stable opening/closing device generally referred to at reference numeral 108 for automatically performing an opening or closing movement of the tray 102 and securing the tray 102 in closed position. Specifically, the bi-stable opening/closing device 108 comprises a central turning knuckle 97 for rotatably supporting a first arm 98 and a second arm 99 around a central axis 109 radially projecting from the turning knuckle 97. The turning knuckle 97 is slidably supported by means of a horizontal guiding rod 100 in parallel alignment with respect to the guiding rails 113 of the supporting base 103. At their free ends, the two arms 98, 99 are inter-connected by a coil spring 101. The tray 102 can be releasably connected to the opening/closing device 108 by means of an elastically deformable spring catch 107 fixed to the supporting base 103. Specifically, the spring catch 107 forms a deepened resting portion 114 for engagement with a projection 112 fixed to the opening/closing device 108 so as to be movable with the turning knuckle 97. The instrument 1 further includes a lever 91 fixedly secured to the instrument 1 at fulcrum 92. On the one side of the fulcrum 92, the lever 91 has an upper lever portion 93 which, at its upper end 95, is coupled to the vertically movable detector module 6 by means of connecting rod 96. On the other side of the fulcrum 92, the lever 91 has a lower lever portion 94 which, at its lower end 110, is coupled to the horizontally movable turning knuckle 97.

Figure 9A:
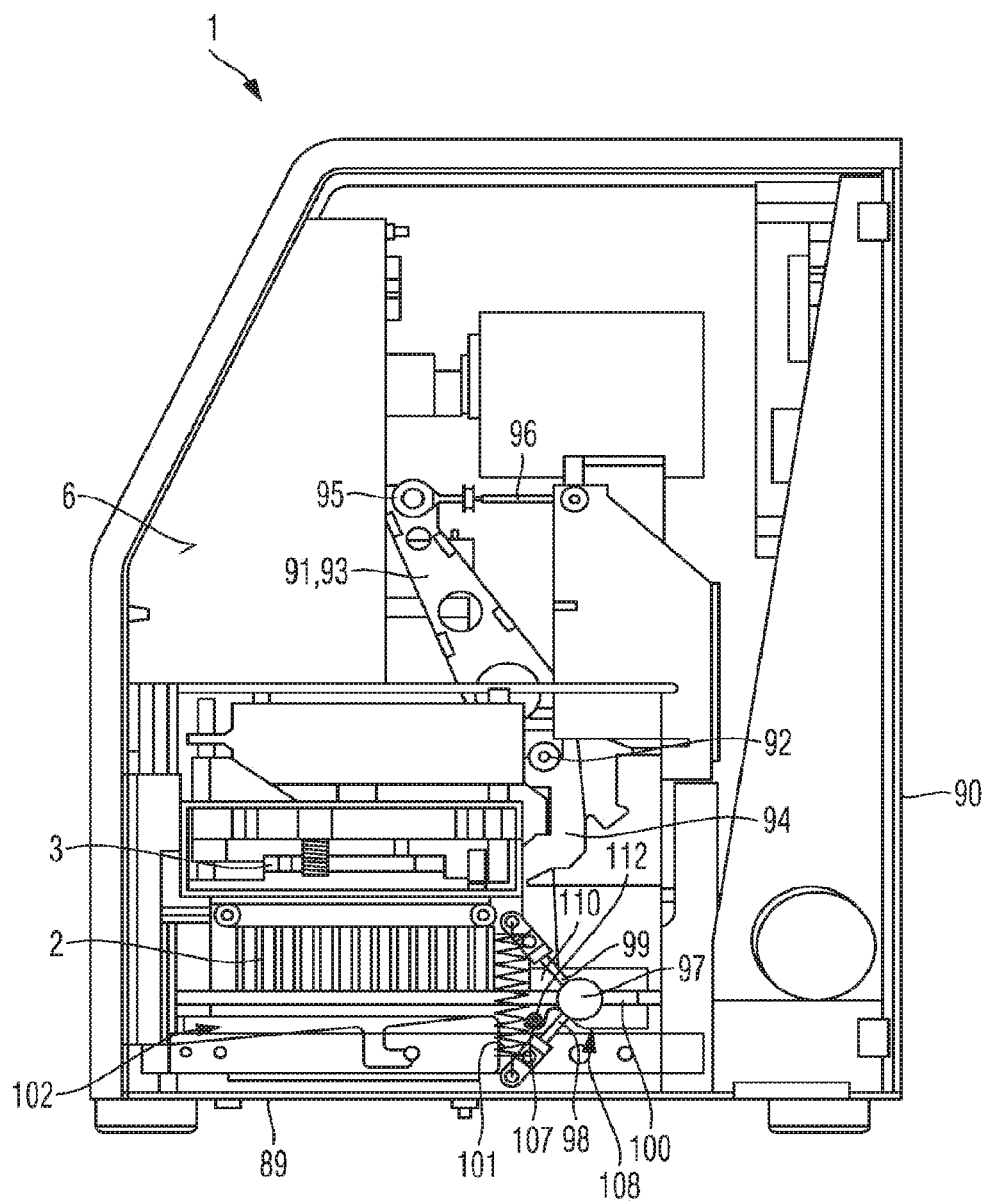
FIGS. 9A-9F are perspective views illustrating a tray for moving the thermal module of the instrument of FIGS. 2 to 8.
Figure 10:
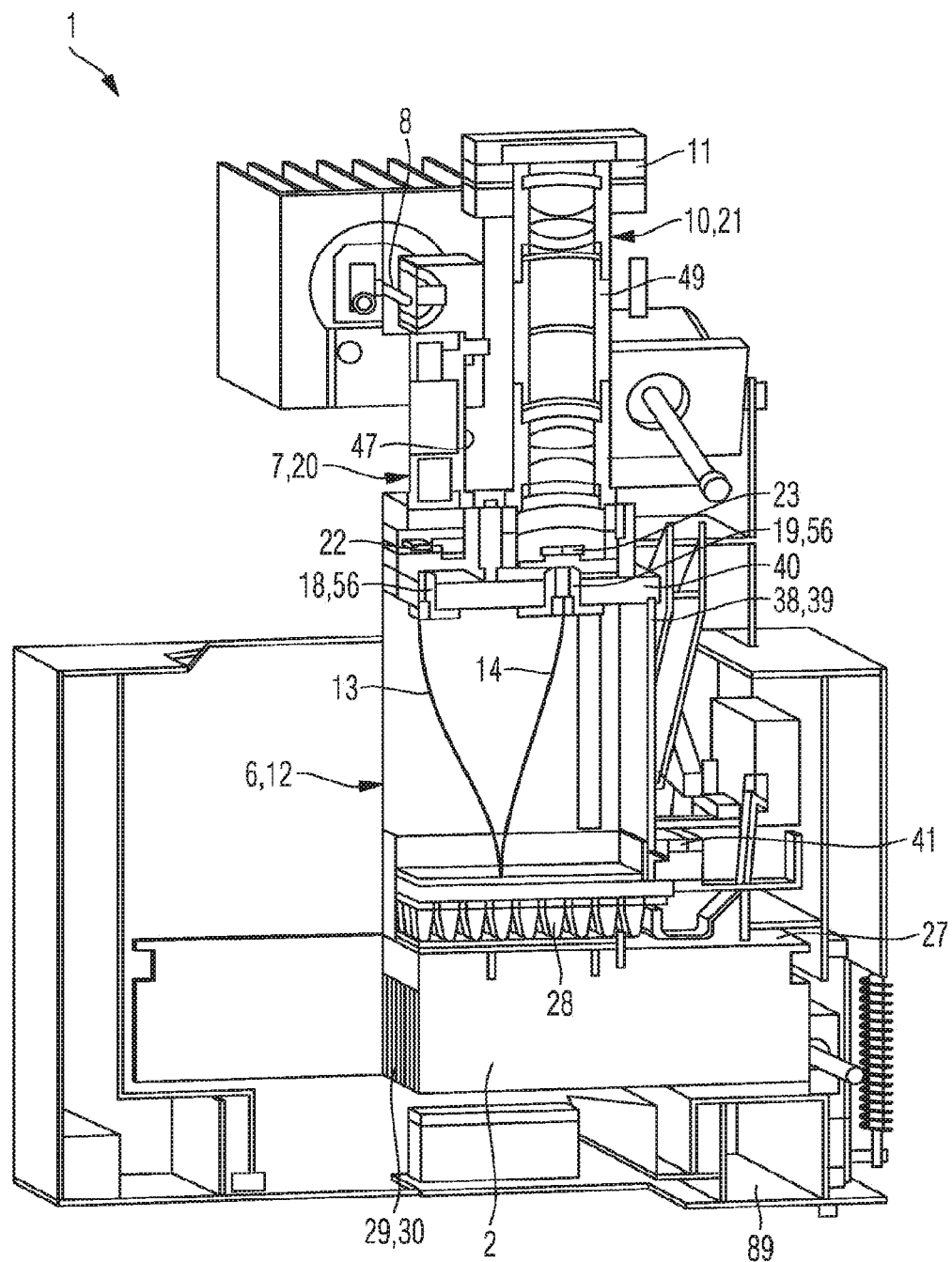
FIG. 10 is a partly sectioned perspective view of another exemplary instrument the modules of which are schematically illustrated in FIG. 1.

With particular reference to FIG. 9A, a situation is depicted where the thermal module 2 is in processing position inside the instrument casing 90 for thermally treating the samples 5. In this situation, the detection module 6 is in the lowered operative position, e.g., applying a force on the multi-well plate 3, for detecting the emitted light 24. The two arms of the bi-stable opening/closing device 108 are in a first stable position on the one side (in FIG. 9A, e.g., the left side) of the turning knuckle 97, in which the free ends thereof are elastically connected by the coil spring 101. In the first stable position, the two arms 98, 99 form an angle of about 90 degrees which can readily be reached by stoppers (not illustrated) for stopping the rotational movement of the arms 98, 99. In this situation, the tray 102 is connected to the opening/closing device 108 by means of the spring catch 107 engaged with the projection 112 which rests in the resting portion 114 of the spring catch 107. Accordingly, the tray 102 is secured against inadvertent manual opening since the elastic force of the coil spring 101 has to be overcome when the tray 102 is to be opened.

Figure 9B:
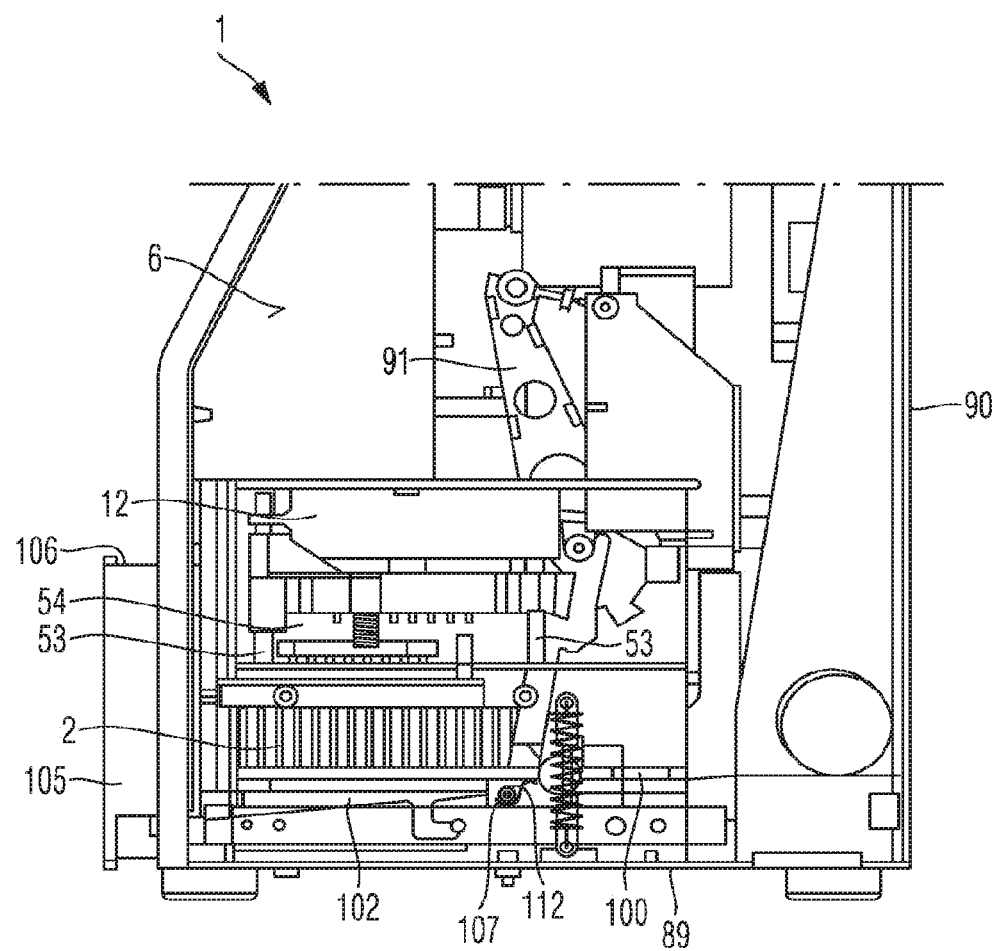
Figure 9C:
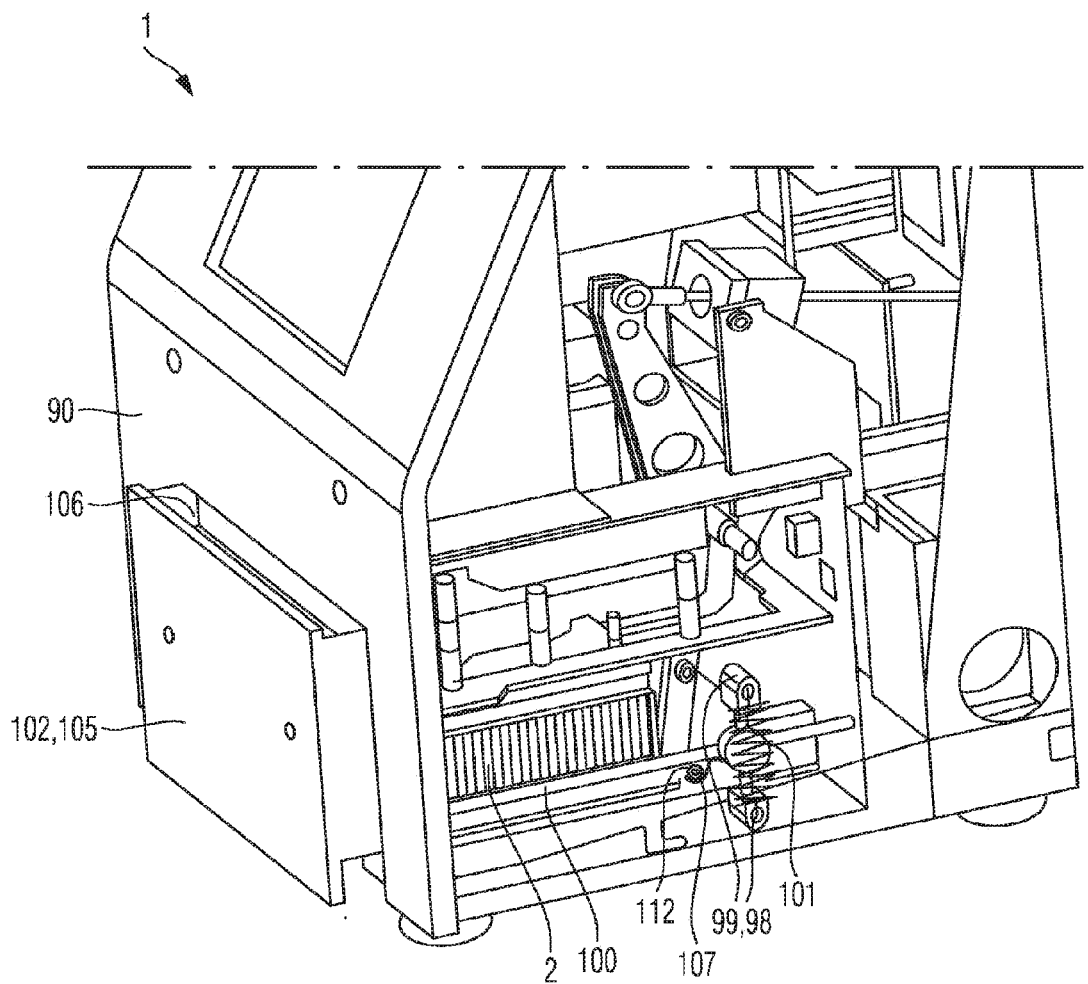

With particular reference to FIGS. 9B and 9C, another situation is depicted in two perspective views where the detection module 6 has been brought in the vertically raised inoperative position by means of the vertical moving mechanism 52. In inoperative position, the detection module 6 is distanced from the thermal module 2 so as to create the free space 54 there-between. When moving the detection module 6 in vertical direction, the lever 91 is turned at the fulcrum 92 (in FIGS. 9B and 9C, e.g., in clockwise direction) so that the turning knuckle 97 is moved along the guiding rod 100 (e.g. to the left side) by means of the lower lever portion 94 coupled to the turning knuckle 97. Being coupled to the projection 112, the tray 102 is simultaneously moved in horizontal direction (in FIGS. 9B and 9C to the left side) so that a recessed grip 106 for manually gripping the tray 102 formed by the upper side of the front cover 105 becomes accessible from outside. Otherwise, when raising the detection module 6, the two arms 98, 99 are rotated beyond an instable position in which they extend in opposite directions elastically expanding the coil spring 101.

Figure 9D:
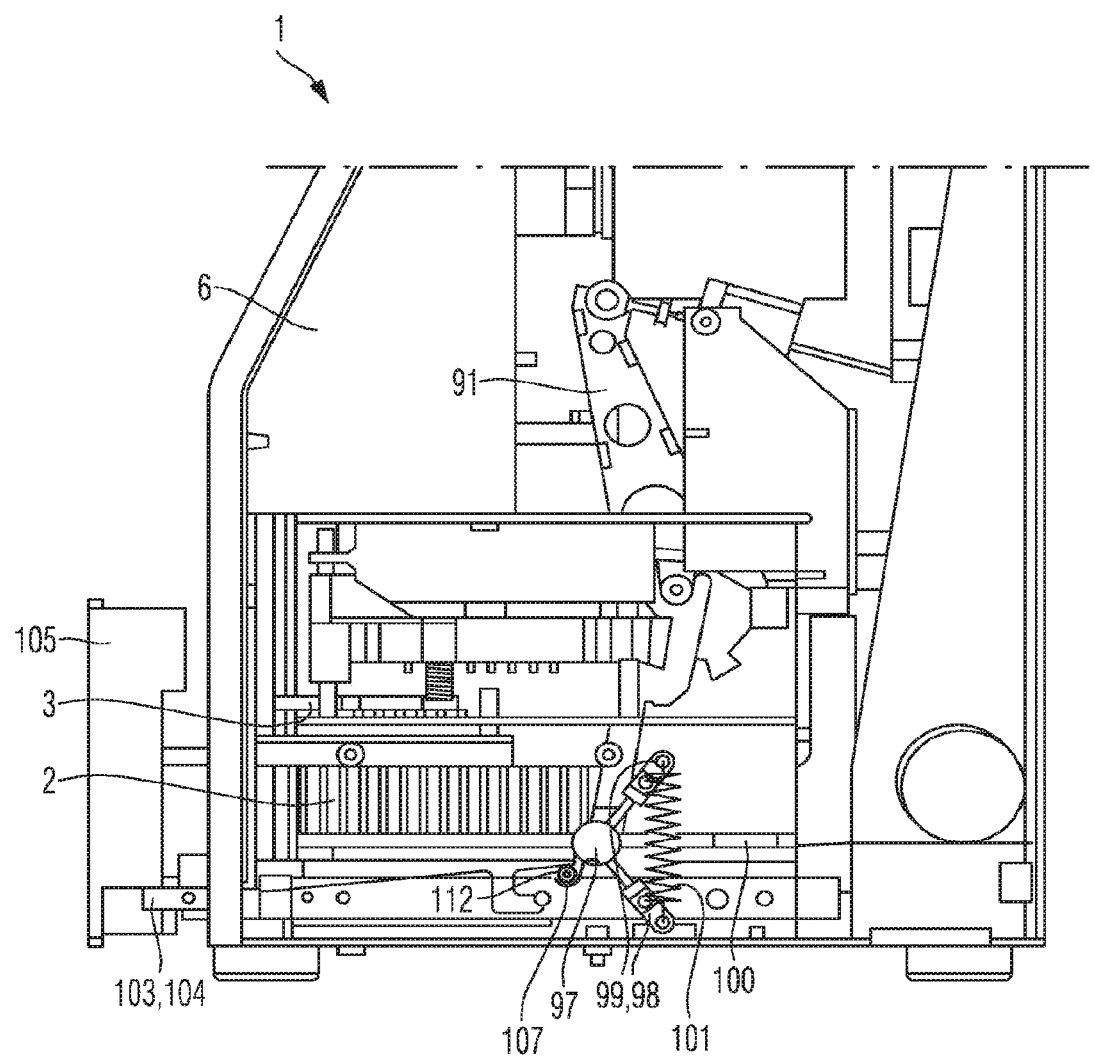
Figure 9E:
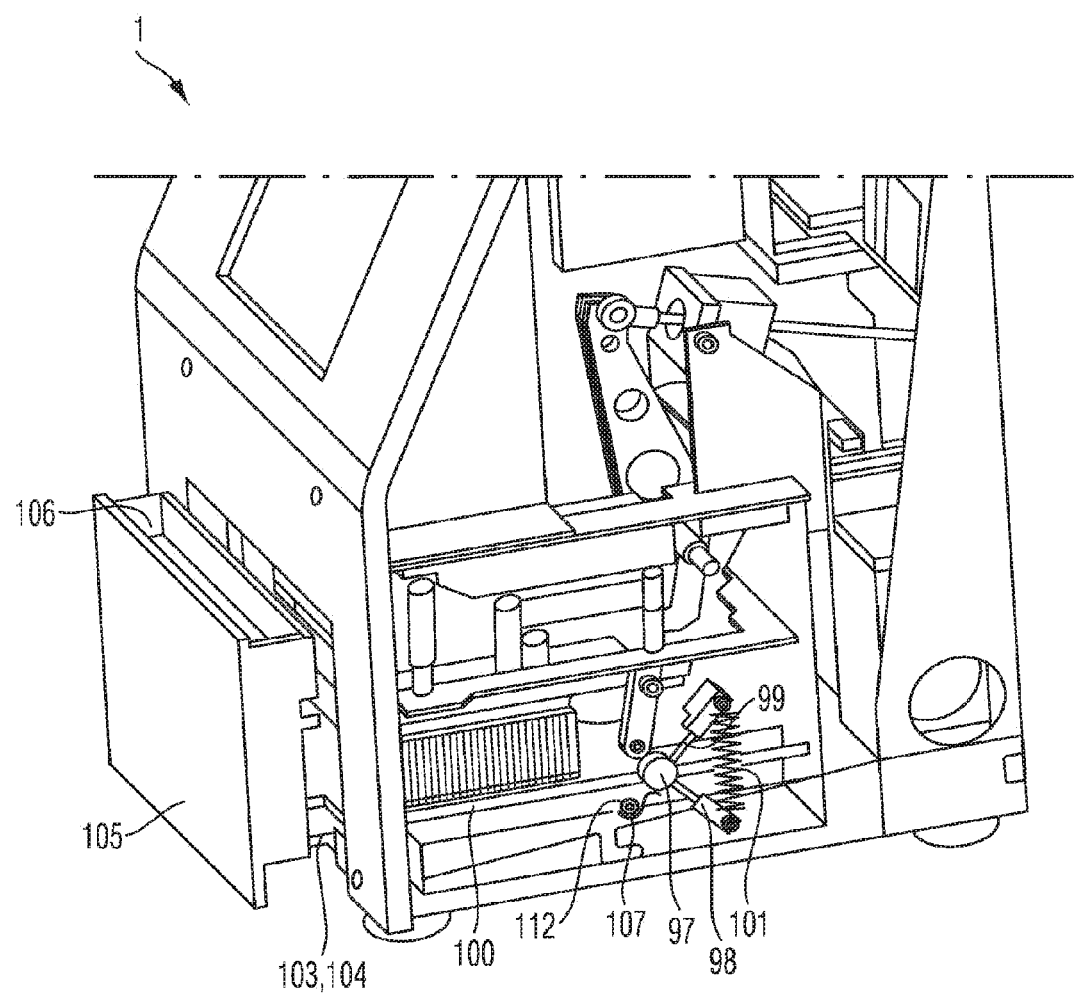

With particular reference to FIGS. 9D and 9E, driven by the elastic force of the contracting coil spring 101, the two arms 98, 99 are brought in a second stable position on the other side (in FIGS. 9D and 9E, e.g., the right side) of the turning knuckle 97. In the second stable position, the free ends of the arms 98, 99 are elastically connected by the coil spring 101 which again form an angle of about 90 degrees which can readily be reached by stoppers for stopping rotational movement of the arms (not shown). As a result, the tray 102 coupled to the opening/closing device 108 by the spring catch 107 is moved in a position where the recessed grip 106 is fully accessible from outside.

Figure 9F:
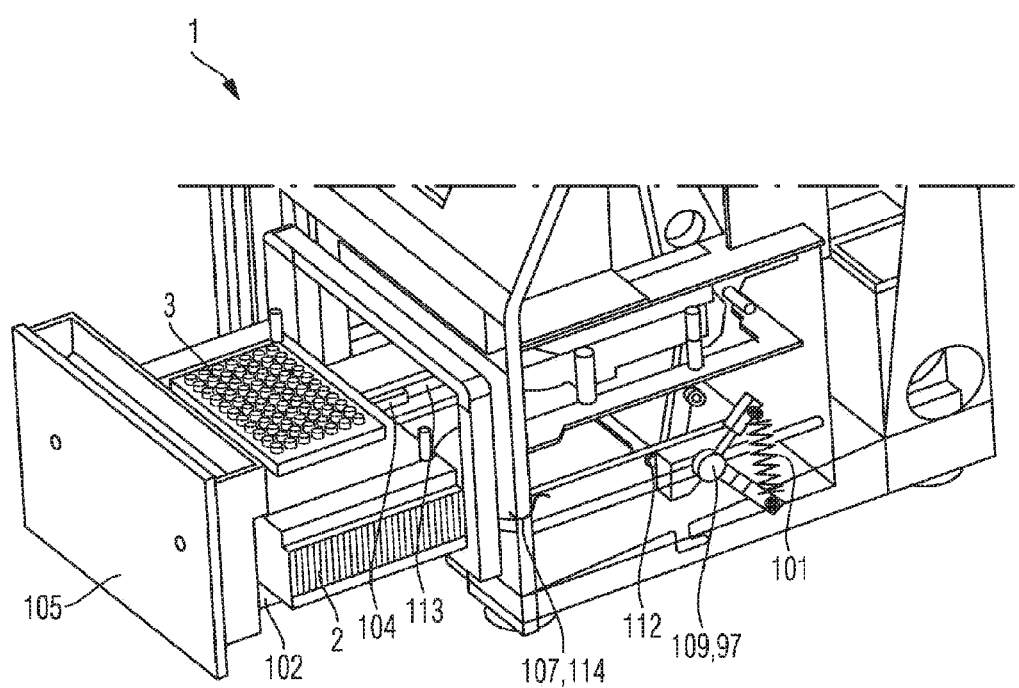

With particular reference to FIG. 9F, by manually gripping the recessed grip 106, the tray 102 can be drawn out of the instrument casing 90 to be brought in the charging/uncharging position for charging the multi-well plate 3 on the receptacle 28 of the thermal module 2 or removing it therefrom. When manually moving the tray 102 in the charging/uncharging position, the spring catch 107 gets out of engagement with the projection 112 by counteracting the elastic force of the spring catch 107 so that the tray 102 is released from the bi-stable opening/closing device 108.

Otherwise, the supporting base 103 can readily be returned into the instrument casing 90 by the reverse action. Accordingly, the tray 102 is manually pushed at the recessed grip 106 into the instrument casing 90 until the spring catch 107 gets in engagement with the projection 112, and is further pushed to the inside so as to move the turning knuckle 97 along the guiding rod 100 (e.g. to the right side) until the two arms 98, 99 are rotated beyond the instable position in which they extend in opposite directions elastically expanding the coil spring 101. Now driven by the elastic force of the contracting coil spring 101, the two arms 98, 99 are brought in the first stable position causing the tray 102 to be automatically moved into the closed position where the front cover 105 closes the instrument casing 90 and the thermal module 2 is in processing position.

In some embodiments, the wells 4 are pre-filled with the samples 5 before being charged into the instrument 1. In some embodiments, the wells 4 are filled with the samples 5 when the multi-well plate 3 is located on the receptacle 28. In some embodiments, the samples 5 are put through various temperature excursions to thereby incubate reaction mixtures contained therein at predefined temperatures for predefined incubation intervals, e.g., for performing the polymerase chain reaction. The temperature of the samples 5 may, e.g., be raised to around 90° C. for melting the nucleic acids and lowered to approximately 40° C. to 70° C. for primer annealing and primer extension along the denaturated polynucleotide strands. In some embodiments, melting of the nucleic acids is performed wherein, e.g., fluorescence light of the samples 5 is detected while the temperature of the samples 5 is slowly risen or lowered. A typical melting curve may start between 30° C. and 50° C. and may end between 75° C. and 95° C. wherein ramp rates in a range of from 0.05 to 0.25° C./sec can, e.g., be used.

The instrument 1 for the automated thermo-cycling of samples 5 can be made highly-compact permitting the use of short optical fibers 13, 14. The first end faces 60 of the fixed first end portions 15 of the optical fibers 13, 14 can be brought very close to the transparent sealing cover 34 so as to improve the sensitivity of the optical detection of the emitted light 24 while avoiding any direct contact between the fibers 13, 14 and the sealing cover 34. In some embodiments, a (vertical) distance between the first end faces 60 and the transparent sealing cover 34 is in the range of from 0.5 to 5 mm, preferably in the range of from 1 mm to 3 mm.

In some embodiments, the instrument 1 can be operated to perform real-time (on-line) detection of the emitted light 24 so as to identify reaction products of the samples 5, e.g., in parallel for all samples 5 even during progress of the thermal treating. Particularly, in some embodiments, the samples 5 can be thermally cycled while synchronously detecting the emitted light 24 for all samples 5 in parallel. Otherwise, in some embodiments, due to the paired optical fibers 13, 14, coupling of the excitation light 9 into the excitation fibers 13 and coupling of the emitted light 24 out of the emission fibers 14 can be performed synchronously and in parallel for all samples 5.

As illustrated in FIG. 10, illustrating another exemplary instrument 1, in some embodiments, both the excitation and detection arrangement 7, 10 are arranged to have a vertical path of rays, wherein the excitation arrangement 7 includes only one light source 8 optically coupled to one or more excitation filters 22 for filtering the excitation light 9. Accordingly, there is no need for using a dichroic mirror as depicted in FIG. 2 for illuminating the samples 5.

Figure 11:
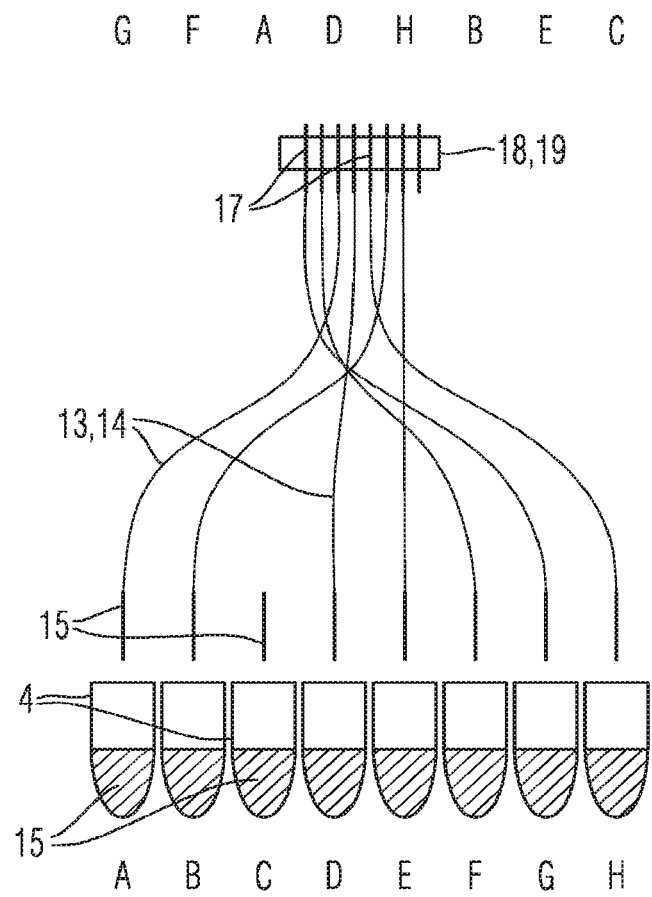
FIG. 11 illustrates a one-to-one connection between the first and second end portions of the optical fibers of the instruments of FIGS. 2 to 10.
Figure 12:
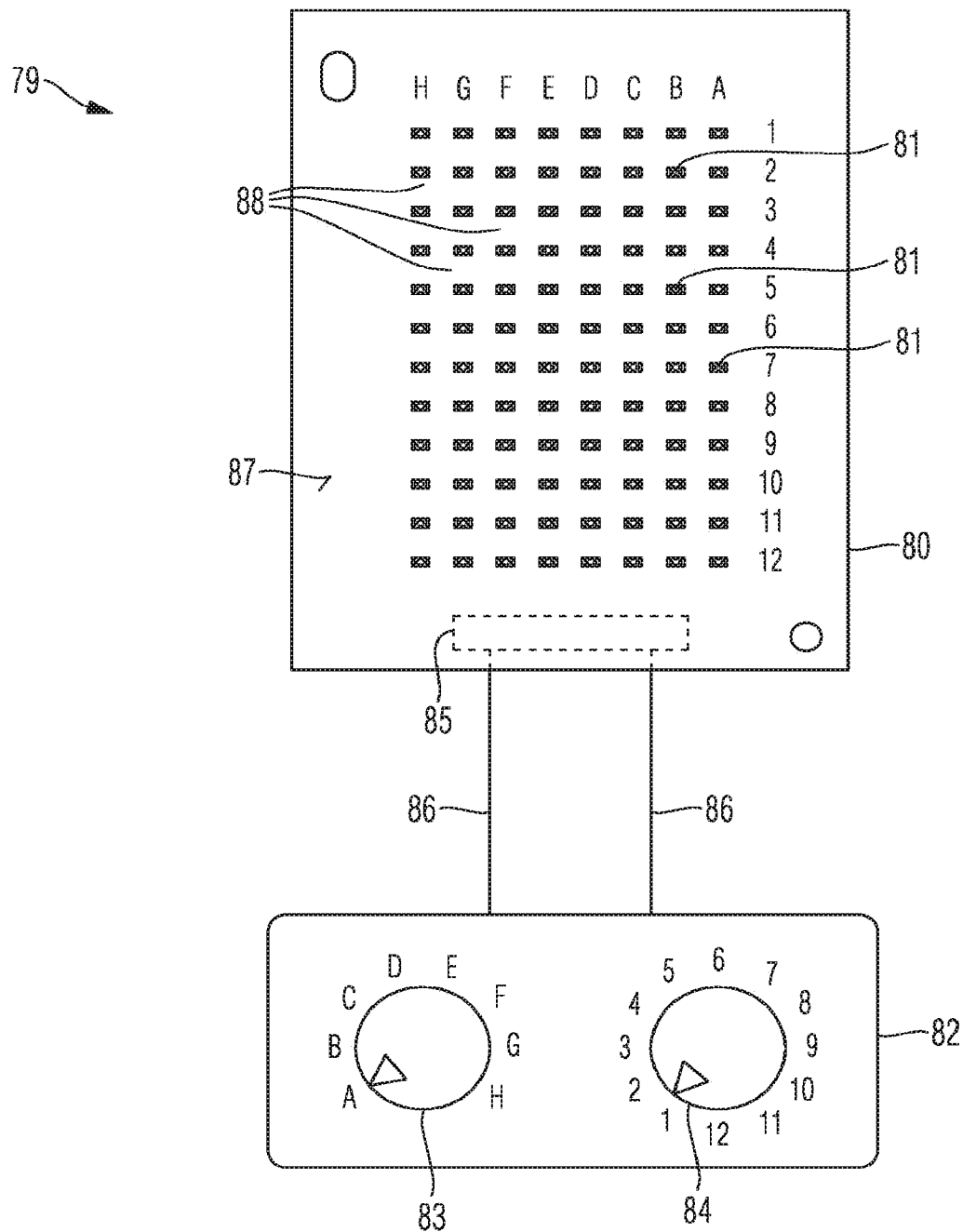
FIG. 12 illustrates a device for mapping the first and second ends of the optical fibers of the instruments of FIGS. 2 to 10.

Reference is now made to FIGS. 11 and 12 to illustrate an exemplary method for determining a one-to-one relationship between the first and second end portions 15, 17 of the optical fibers 13, 14 of the instrument 1. With particular reference to FIG. 11, in some embodiments, the first end portions 15 of the optical fibers 13, 14 are fixed with respect to each other by the first fixing element 16 (not illustrated in FIG. 11) while the second end portions 17 of the excitation fibers 13 are fixed with respect to each other by the second fixing element 18 and the second end portions 17 of the emission fibers 14 are fixed with respect to each other by the third fixing element 19. In FIG. 11, one type of optical fibers 13, 14 is depicted for the purpose of illustration only while it is to be appreciated that FIG. 11 similarly applies to both excitation and emission fibers 13, 14.

In some embodiments, there is a stochastic or random arrangement of the first and second end portions 15, 17 of the optical fibers 13, 14 in each of the first to third fixing elements 16, 18, 19 considerably facilitating the production thereof. This is because no specific scheme or ordering has to be observed during the production. Hence, with respect to the first end portions 15 of the optical fibers 13, 14 which in operative position of the detection module 6 are in a position to establish a one-to-one relationship between the first end portions 15 and the wells 4 and, e.g., are located right above the wells 4, it initially is not apparent into which well 4 the excitation light 9 exiting the first end portions 15 of the excitation fibers 13 is being directed, and, typically more important, by which sample 5 the emitted light 24 exiting specific second end portions 17 of the emission fibers 14 has been generated. For instance, the emitted light 24 of a serial arrangement of eight wells 4 denoted as A, B, C, D, E, F, G and H can be detected by a serial arrangement of second end portions 17 of the emission fibers 14 G, F, A, D, H, B, E and C. Hence, without knowing the exact mapping (one-to-one relationship) between the first end portions 15 of the emission fibers 14 and the second end portions 17 thereof, the samples 5 cannot be individually (selectively) detected. In order to overcome such drawback, the mapping between the first and second end portions 15, 17 of each of the optical fibers 13, 14 have to be determined.

With particular reference to FIG. 12, in some embodiments, a device 79 for determining the mapping between the first and second end portions 15, 17 of the optical fibers 13, 14 (in the following denoted as "mapping device") is used. As illustrated, in some embodiments, the mapping device 79 comprises a planar plate-like base 80 having an upper base face 87 provided with a rectangular array of plural light generating elements 81 such as, but not limited to diodes. In some embodiments, the number and arrangement of the light generating elements 81 correspond to the wells 4 of the multi-well plate 3. In some embodiments, the light generating elements 81 are arranged in plural parallel columns and plural parallel rows intersecting each other at right angles. As illustrated, in some embodiments, the mapping device, e.g., includes eight columns A-H and twelve rows 1-12 of light generating elements 81 depending on the multi-well plate 3 used in the instrument 1.

With continued reference to FIG. 12, in some embodiments, the mapping device 79 further comprises a control panel 82 and is equipped with two manually operable turn-switches 83, 84. Specifically, in some embodiments, a first turn switch 83 can be used for setting a specific column A-H and a second turn switch 84 can be used for setting a specific row 1-12. In some embodiments, the control panel 82 is being connected to a device controller 85 fixed on the underside of the base 80 for controlling the light generating elements 81 by means of electric lines 86. As set by the turn-switches 83, 84, the light generating elements 81 can selectively be supplied with electric current to generate light.

With yet continued reference to FIG. 12, in some embodiments, the base 80 is configured to be placed on the receptacle 28 instead of the multi-well plate 3 in such a manner that the detection module 6 can be moved in operative condition. In some embodiments, the first end portions 15 of the emission fibers 14 are located right above the light generating elements 81 in such a manner that each first end portion 15 is related to a separate light generating element 81. In some embodiments, the lower contact face 37 of the heating plate 66 contacts the upper base face 87 in contact areas 88 in-between the light generating elements 81 so that each light generating element 81 is accommodated in a separate cover heater hole 78. Accordingly, in some embodiments, the light generating elements 81 are optically shielded with respect to each other in case the contact face 37 contacts the upper base face 87.

Accordingly, knowing the exact position of each of the light generating elements 81 as given by its column and row, in some embodiments, the light generating elements 81 are consecutively supplied with electric current to generate light that is coupled into the first end portions 15 of the emission fibers 14 and coupled out at the second end portions 17 thereof. Accordingly, by means of the detectors 11 detecting the light of the light generating elements 81, a one-to-one relationship (mapping) between the first end portions 15 of the emission fibers 14 or wells 4 and the second end portions 17 can readily be established. In some embodiments, this one-to-one relationship is saved in a, e.g. permanent, data storage 115, e.g., in the form of a look-up table so as to enable the wells 4 or samples 5 contained therein to be selective detected.

As above-detailed, in some embodiments, a picture of the second end faces 61 of the second end portions 17 of the emission fibers 14 is obtained by the detectors 11 without having a one-to-one mapping between the second end faces 61 and the pixels of the detectors 11. Otherwise, electronic picture processing, e.g., based on the known one-to-one relationship (mapping) between the first and second end portions 15, 17 of the emission fibers 14 can be used to obtain information about the relationship between the pixels of the detectors 11 and the second end faces 61 of the emission fibers 14 so as to attribute the detected light to individual wells 4.

Figure 13:
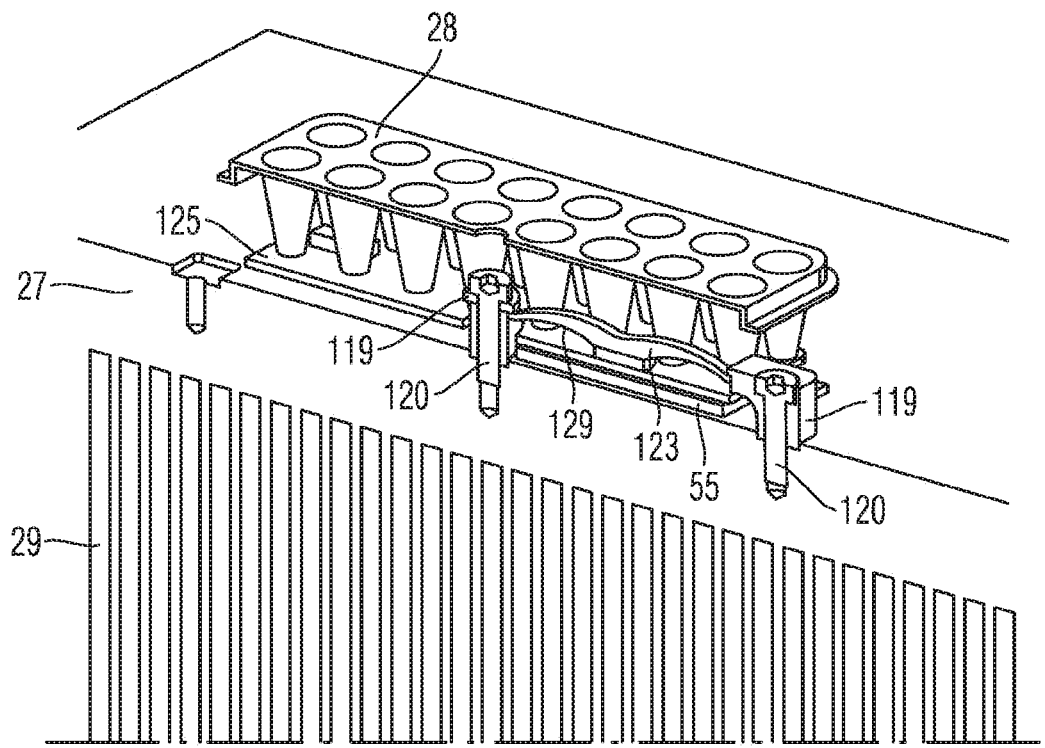
FIG. 13 is a sectional view illustrating a clamping mechanism for clamping the receptacle of the instruments of FIGS. 2 to 10.
Figure 14:
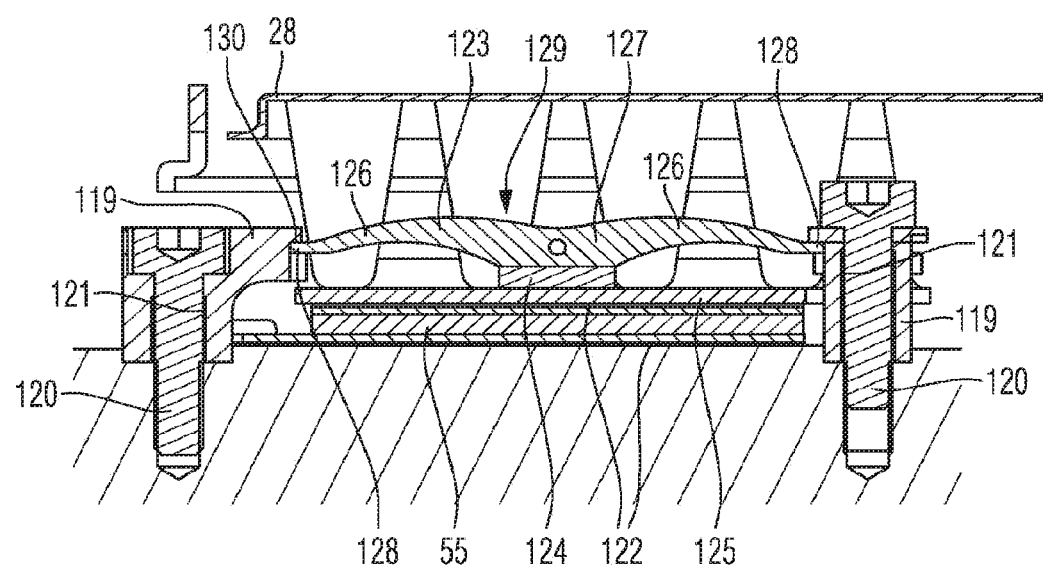
FIG. 14 illustrates an enlarged detail of FIG. 13.
Figure 15:
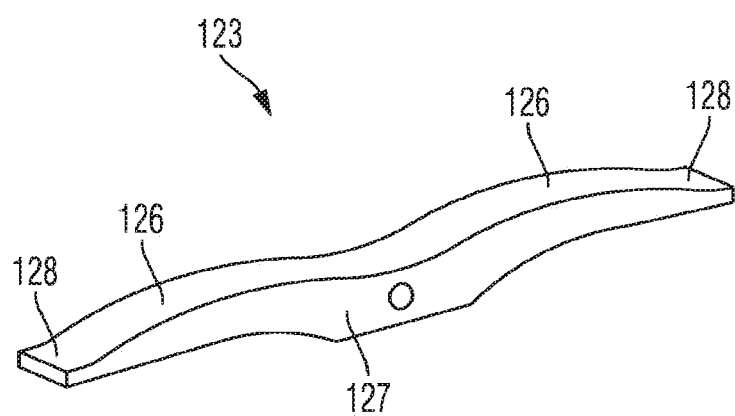
FIG. 15 is a perspective view illustrating the clamp of FIGS. 13 and 14.

With particular reference to FIGS. 13 to 15, a clamping mechanism 129 for clamping the receptacle 28 of the instruments 1 of FIGS. 2 to 10 is described. As a matter of fact, in some embodiments such as, but not limited to, the case of using the instrument 1 as thermo-cycler, the receptacle 28 is required to have a temperature distribution as homogeneous as reasonably possible. In order to meet this requirement, the receptacle 28 is clamped to the one or more thermoelectric devices 55 of the thermal block 27. The clamping mechanism 129 is configured to exert a well-defined force and force distribution to the receptacle 28. Stated more particularly, in some embodiments, the clamping mechanism 129 comprises a resilient clamp 123 made of elastic material such as, but not limited to, spring steel according to DIN regulation 1.4310. In some embodiments, the clamp 123 is configured as flat spring. Specifically, as illustrated, in some embodiments, the clamp 123 is configured as elongate member having two opposing arms 126 connected by a middle portion 127. The middle portion 127 is provided with an isolation block 124 resting on a base plate 125 of the receptacle 28. The isolation block 124 is made of thermally isolating material such as, but not limited to, fiber enforced polymer. Flanges 119 on both sides of the clamp 123 are provided with gripping recesses 130 in gripping engagement with gripping portions 128 of the arms 126. The flanges 119 are fixedly secured to the thermal block 27 by means of screws 120 which can be screwed in and out of mounting holes 121. Accordingly, by turning the screws 120 in, the gripping portions 128 of the arms 126 can be moved towards the base plate 125 while bending the arms 125. As a result, a clamping force is exerted on the base plate 125 via the middle portion 127 to thereby clamp the receptacle 28 to the one or more thermoelectric devices 55 to thereby equalize mechanical tolerances. As illustrated, in some embodiments, a further homogenization of the clamping force and thus temperature distribution can be reached by one or more interface layers 122 on one or both sides of the thermoelectric devices 55 made of material having good thermal conductivity such as, but not limited to, oil, paste or foil adapted for heat transfer. The thermal isolation block 124 inhibits excessive heat-flow from the receptacle 28 towards the thermal block 27 by means of the clamp 123, e.g., in a case when the receptacle 28 is heated to a temperature of, e.g., 95° C. and the thermal block 27 has a lower temperature of, e.g., 35° C. In some embodiments, e.g., for a thermoelectric device 55 having an area of about 16 cm2, the clamp 123 is configured to exert a clamping force in a range of from 200 N to 500 N. Those of skill in the art, however, will appreciate that the clamping force exerted on the receptacle 28 may vary according to the specific demands of the user and, in some embodiments, can for instance be in a range of from 10 N to 1000 N. In some embodiments, instead of one clamping mechanism 129, the instrument 1 includes plural clamping mechanisms 129 for clamping the receptacle 28 to the thermoelectric devices 55.

Obviously many modifications and variations of the present invention are possible in light of the above description. It is therefore to be understood, that within the scope of appended claims, the invention may be practiced otherwise than as specifically devised. Some examples: in some embodiments, the excitation and detection arrangements 7, 10 are not integrally formed with the coupling arrangement 12 permitting the light-weight coupling arrangement 12 to be vertically moved into operative position for treating the samples 5 or inoperative position for charging/un-charging the multi-well plate 3 while keeping the excitation and detection arrangements 7, 10 unmoved. This requires the second end faces 61 of the fibers 13, 14 to be optically coupled to the excitation and detection arrangements 7, 10. In some embodiments, the detection module 6 is laterally arranged as to the thermal module 2 so that the constructional height can be reduced. In some embodiments, instead of a pair of optical fibers 13, 14 per well 4, only one optical fiber is used for transmitting both the excitation and emission light. In these cases, the excitation and emitted light can be optically de-coupled by means of a dichroic mirror. In some embodiments, a bundle of optical fibers 13, 14 per well 4 is used for transmitting the excitation and emitted light 9, 24. In some embodiments, instead of being perpendicularly arranged with respect to the wells 4, the first through-holes 42 are inclined with respect to a (e.g. horizontal) opening face of the wells 4. In some embodiments, instead of accommodating one pair of optical fibers 13, 14 in one through-hole 42, 45, 46, each fiber 13, 14 is accommodated in a separate through-hole so that each pair of excitation and emission fibers 13, 14 is accommodated in two through-holes. In these cases, the through-holes of one pair of optical fibers 13, 14 may, e.g., have a minimum distance of 0.2 mm. This list of modified embodiments is not exhaustive.

What is claimed is:

1. An instrument for the automated thermal treatment of liquid samples, comprising:
   a temperature-controlled receptacle configured to be loaded with a plurality of vessels for containing said samples, said receptacle being configured to form a thermal communication with said loaded vessels;
   a detection module equipped with a detection arrangement provided with one or more detectors configured to detect light emitted from said samples and a coupling arrangement provided with a plurality of optical fibers configured to transmit said emitted light to said detection arrangement, wherein said optical fibers have first and second end portions, said first end portion and said second end portion of each optical fiber being fixed with respect to each other; and
   a moving mechanism configured to move said coupling arrangement and/or said receptacle to vary an inter-distance between said coupling arrangement and said receptacle so as to allow the vessels to be loaded to or unloaded from said receptacle and to allow detection of light from samples contained in said one or more receptacle-loaded vessels;
   wherein the second end portions have a stochastic lateral position and wherein a mapping between said first end portion and said second end portion of individual optical fibers is being stored in a data storage.

2. The instrument of claim 1, wherein the moving mechanism is configured to move the coupling arrangement while the receptacle is being kept stationary.

3. The instrument of claim 1, wherein the moving mechanism is configured to move the coupling arrangement while the detection arrangement is being kept stationary.

4. The instrument of claim 1, wherein the moving mechanism is configured to move the detection module.

5. The instrument of claim 4, wherein the moving mechanism is configured so that the detection module can selectively be moved into a lowered first or operative position adapted for optically detecting reaction products obtained from samples or in a raised second or inoperative or loading/unloading position adapted for loading or unloading the instrument.

6. The instrument of claim 1, wherein the fixation of the first end portion and the second end portion of each optical fiber with respect to each other avoids mechanical forces acting on the optical fibers during a vertical movement of the detection module.

7. The instrument of claim 1, wherein the fixation of the first end portion and said second end portion of each optical fiber with respect to each other avoids changes of the shape of the optical fibers during variation of the inter-distance between said coupling arrangement and said receptacle.

8. The instrument of claim 1, wherein coupling arrangement comprises a rigid chassis.

9. The instrument of claim 8, wherein the rigid chassis includes an upper horizontal plate and spaced-apart lower horizontal plates.

10. The instrument of claim 9, wherein a first fixing element for fixing the first end portions of the optical fibers is a solid plate fixed to the lower horizontal plates so as to be integrally formed with the chassis.

11. The instrument of claim 9, wherein second and third fixing elements for fixing the second end portions of the optical fibers are fixed to the upper horizontal plate.

12. The instrument of claim 9, wherein the excitation arrangement is accommodated in a first casing which is fixed to an upper face of the upper horizontal plate.

13. The instrument of claim 9, wherein the detection arrangement is accommodated in a second casing which is fixed to an upper face the upper horizontal plate.

14. The instrument of claim 1, wherein the detection module further comprises an excitation arrangement provided with one or more light sources for generating excitation light.

15. The instrument of claim 1, wherein the instrument includes a horizontally movable tray comprising a horizontal supporting base supporting a thermal module configured to receive a multi-well plate.

16. An instrument for the automated thermal treatment of liquid samples, comprising:
a temperature-controlled receptacle configured to be loaded with a plurality of vessels for containing said samples, said receptacle being configured to form a thermal communication with said loaded vessels;
a detection module equipped with a detection arrangement provided with one or more detectors configured to detect light emitted from said samples and a coupling arrangement provided with a plurality of optical fibers configured to transmit said emitted light to said detection arrangement, wherein said optical fibers have first and second end portions, said first end portion and said second end portion of each optical fiber being fixed with respect to each other; and a moving mechanism configured to move said coupling arrangement and/or said receptacle to vary an inter-distance between said coupling arrangement and said receptacle so as to allow the vessels to be loaded to or unloaded from said receptacle and to allow detection of light from samples contained in said one or more receptacle-loaded vessels, wherein the fixation of the first end portion and the second end portion of each optical fiber with respect to each other avoids mechanical forces acting on the optical fibers during a vertical movement of the detection module.

17. An instrument for the automated thermal treatment of liquid samples, comprising:
a temperature-controlled receptacle configured to be loaded with a plurality of vessels for containing said samples, said receptacle being configured to form a thermal communication with said loaded vessels;
a detection module equipped with a detection arrangement provided with one or more detectors configured to detect light emitted from said samples and a coupling arrangement provided with a plurality of optical fibers configured to transmit said emitted light to said detection arrangement, wherein said optical fibers have first and second end portions, said first end portion and said second end portion of each optical fiber being fixed with respect to each other; and a moving mechanism configured to move said coupling arrangement and/or said receptacle to vary an inter-distance between said coupling arrangement and said receptacle so as to allow the vessels to be loaded to or unloaded from said receptacle and to allow detection of light from samples contained in said one or more receptacle-loaded vessels, wherein the fixation of the first end portion and said second end portion of each optical fiber with respect to each other avoids changes of the shape of the optical fibers during variation of the inter-distance between said coupling arrangement and said receptacle.

* * * * *